(12) United States Patent
Marillonnet et al.

(10) Patent No.: US 8,883,420 B2
(45) Date of Patent: Nov. 11, 2014

(54) PROCESS OF CLEAN CLONING

(75) Inventors: Sylvestre Marillonnet, Halle (DE); Stefan Werner, Halle (DE); Carola Engler, Halle/Saale (DE); Romy Kandzia, Halle/Saale (DE); Frank Thieme, Halle/Saale (DE); Ernst Weber, Halle/Saale (DE)

(73) Assignee: Icon Genetics GmbH, Munich (DE)

( * ) Notice: Subject to any disclaimer, the term of this patent is extended or adjusted under 35 U.S.C. 154(b) by 250 days.

(21) Appl. No.: 13/121,019

(22) PCT Filed: Oct. 8, 2009

(86) PCT No.: PCT/EP2009/007237
§ 371 (c)(1),
(2), (4) Date: Jun. 20, 2011

(87) PCT Pub. No.: WO2010/040531
PCT Pub. Date: Apr. 15, 2010

(65) Prior Publication Data
US 2011/0263024 A1    Oct. 27, 2011

(30) Foreign Application Priority Data
Oct. 8, 2008 (EP) ................................. 08017649

(51) Int. Cl.
*C12Q 1/68* (2006.01)
*C12N 15/66* (2006.01)
*C12N 15/64* (2006.01)

(52) U.S. Cl.
CPC ........................... *C12N 15/64* (2013.01); *C12N 15/66* (2013.01)
USPC ........................................ 435/6.12

(58) Field of Classification Search
None
See application file for complete search history.

(56) References Cited

U.S. PATENT DOCUMENTS

2003/0194736 A1* 10/2003 Bitinaite .......................... 435/6
2003/0235814 A1* 12/2003 Bradbury et al. ................ 435/5

FOREIGN PATENT DOCUMENTS

WO    WO/2007/124065   * 11/2007   ............. C12N 15/87
WO    WO 2007/124065 A    11/2007

OTHER PUBLICATIONS

Rapid amplification of 5' complementary DNA ends (5' RACE) (hereinafter, "RACE"; see attached, Aug. 2005).*
Cormack et al. (Rapid amplification of genomic ends (RAGE) as a simple method to clone flanking genomic DNA, Gene, 194(2):273-76, Jul. 31, 1997).*
Li et al. (Ligation independent cloning irrespective of restriction site compatibility, Nucleic Acids Research, 25:20, pp. 4165-4166, 1997).*
Lau et al. (A real-time PCR for SARS-coronavirus incorporating target gene pre-amplification, Biochemical and Biophysical Research Communications, 312:1290-1296, 2003).*
Doenecke et al. (Rapid amplification of cDNA ends (RACE) improves the PCR-based isolation of immunoglobulin variable region genes from murine and human lymphoma cells and cell lines, Leukemia, 11(10):1787-92, Oct. 1997).*
Haun, R. S., et al., "Rapid, Reliable Ligation-Independent Cloning of PCT Products Using Modified Plasmid Vectors," *BioTechniques*, 1992, vol. 13(4), pp. 515-518.
Li, C., et al., "Ligation independent cloning irrespective of restriction site compatibility," *Nucleic Acids Research*, 1997, vol. 25(20), pp. 4165-4166.
Swanson, C., et al., "A directional recombination cloning system for restriction- and ligation-free construction of GFP, DsRed, and lacZ transgenic *Drosophila* reporters," *Gene*, 2008, vol. 408(1-2), pp. 180-186.
Tillett, D., et al., "Enzyme-free cloning: a rapid method to clone PCR products independent of vector restriction enzyme sites," *Nucleic Acids Research*, 1999, vol. 27(19), pp. e26/i-e26/iii.
Betting, D., et al., "Sulfhydryl-Based Tumor Antigen-Carrier Protein Conjugates Stimulate Superior Antitumor Immunity against B Cell Lymphomas," *J Immunol*, 2008, vol. 181, pp. 4131-4140.

* cited by examiner

*Primary Examiner* — Christopher M Babic
*Assistant Examiner* — Aaron Priest
(74) *Attorney, Agent, or Firm* — Alston & Bird LLP

(57) ABSTRACT

A process of inserting a nucleic acid sequence of interest into an acceptor nucleic acid is provided. The process comprises amplifying by PCR a DNA comprising in the following order a sequence segment U, a nucleic acid sequence segment of known nucleotide sequence K2, and a nucleic acid sequence segment of known sequence K3. The process further comprises treating the linear double-stranded DNA molecules from the PCR amplification with an exonuclease to obtain a single-stranded overhang at the first end of the DNA and a single-stranded overhang comprising nucleic acid segments K2 and K3 at the second end of the DNA. The process additionally comprises annealing the product of the exonuclease treatment to a linearized double-stranded acceptor nucleic acid which has been designed to complement the single-stranded overhangs of the product of the exonuclease treatment.

17 Claims, 18 Drawing Sheets

Catching sequence IGHMC3 in pICH36113
for cloning PCR products amplified with Bap2PC and Mu3N (g)ggagtgcat ccgccccaac ccttttcccc ctcgtctcct gtgagaattc cccgtcggat acgagcagcg tggccgttgg Catching sequence IGHMC2 in pICH36101
for cloning PCR products amplified with Bap2PC and Mu2N ctgcctcgca caggacttcc ttcccgactc catcactttg tcctgaaat acaagaacaa ctctgacatc agcagyaccc
→                                                                           ←
Mu3N                                                                        Mu2N ggggcttccc atcagtcctg agagggggca agtacgcagc cacctcacag gtgctgctgc cttccaagga cgtcatgcag ggcacagacg aacacgtggt gtgcaaagtc cagcacccca acggcaacaa agaaaagaac gtgcctcttc ca

Fig. 8

Catching sequence in pICH36083
for cloning PCR products amplified with Bap2PC and KC3N GAACTGTGGC TGCACCATCT GTCTTCATCT TCCCGCCATC TGATGAGCAG TTGAAATCTG GAACTGCCTC TGTTGTGTGC
                                                                              ← KC3N Catching sequence in pICH36078
for cloning PCR products amplified with Bap2PC and KC2N CTGCTGAATA ACTTCTATCC CAGAGAGGCC AAAGTACAGY GGAAGGTGGA TAACGCCCTC CAATCGGGTA ACTCCCAGGA
← KC3N                                                 ← KC2N GAGTGTCACA GAGCAGGASA GCAAGGACAG CACCTACAGC CTCAGCARCA CCCTGACGCT GAGCAAAGCA GACTACGAGA AACACAAAGT CTACGCCTGC GAAGTCACCC ATCAGGGCCT GAGCTCGCCC GTCACAAAGA GCTTCAACAG GGGAGAGTGT

Fig. 9

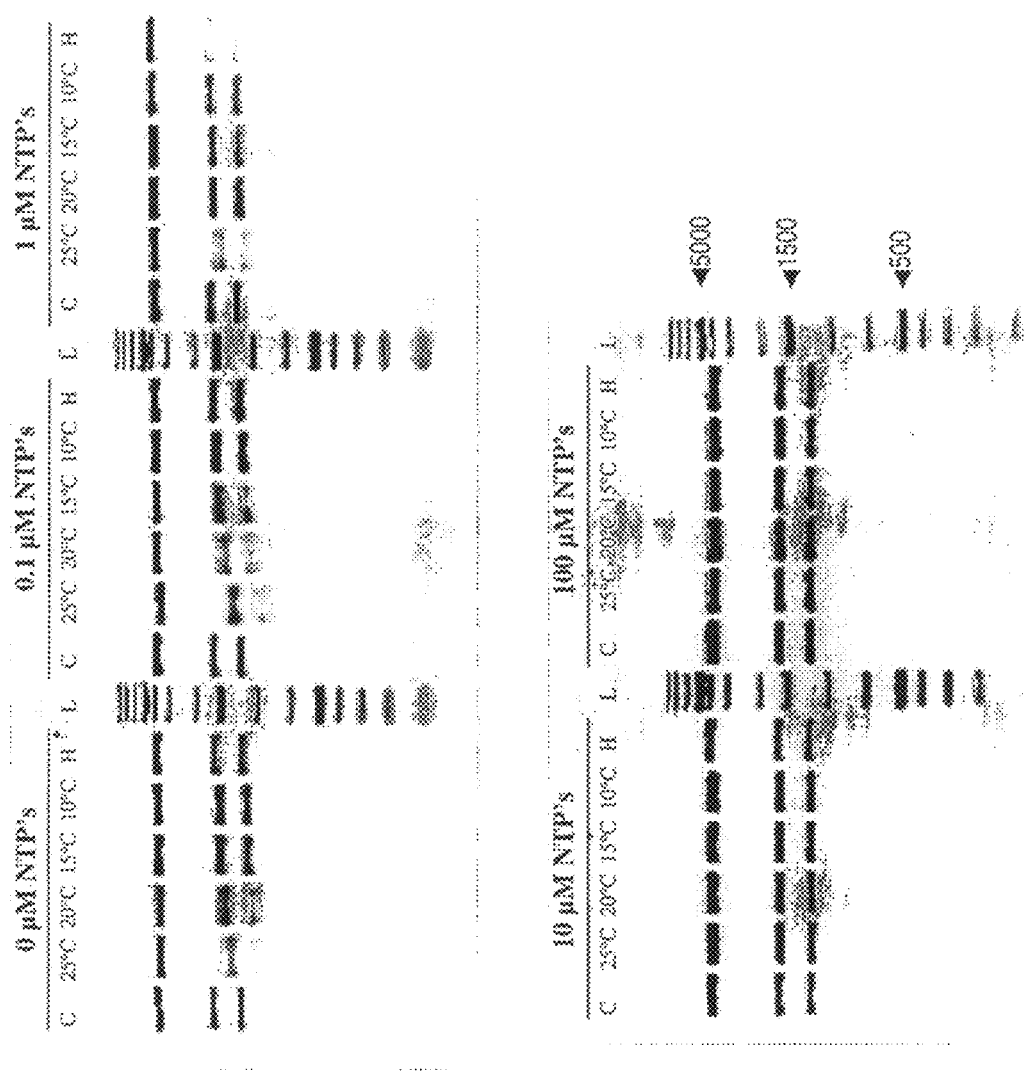

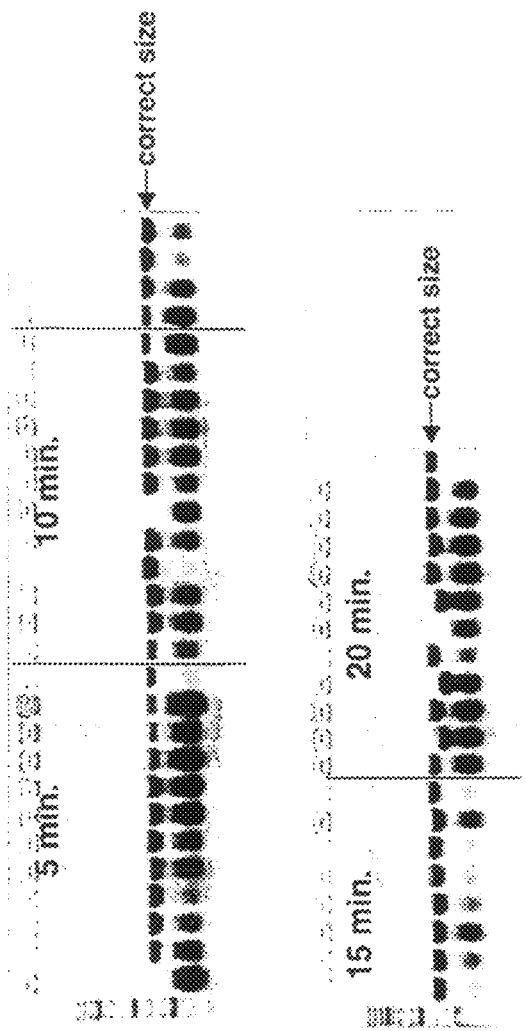
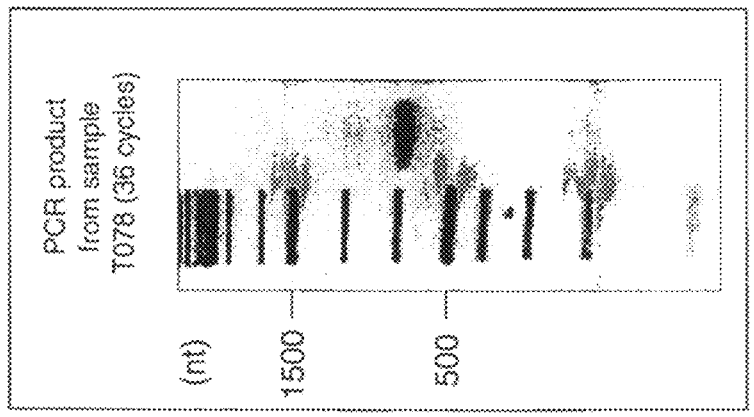
Fig. 11

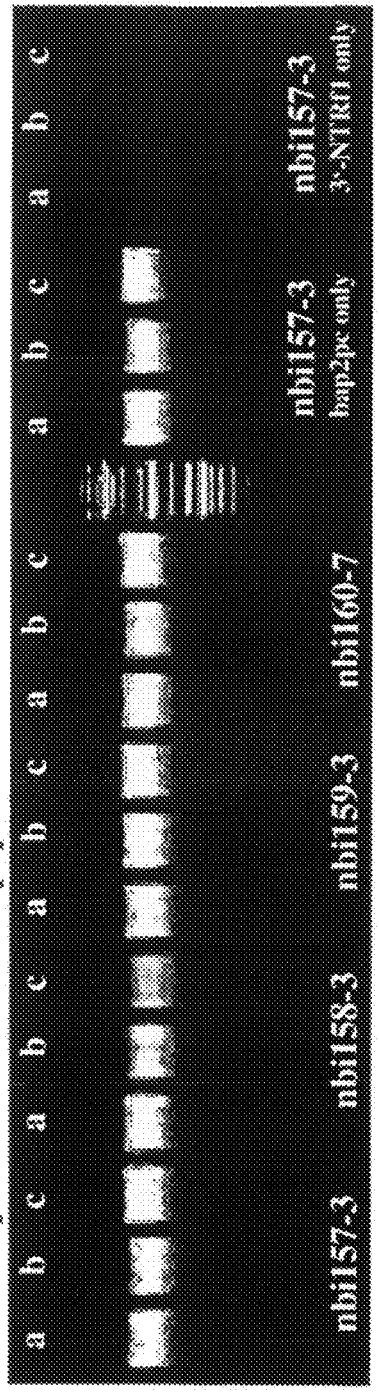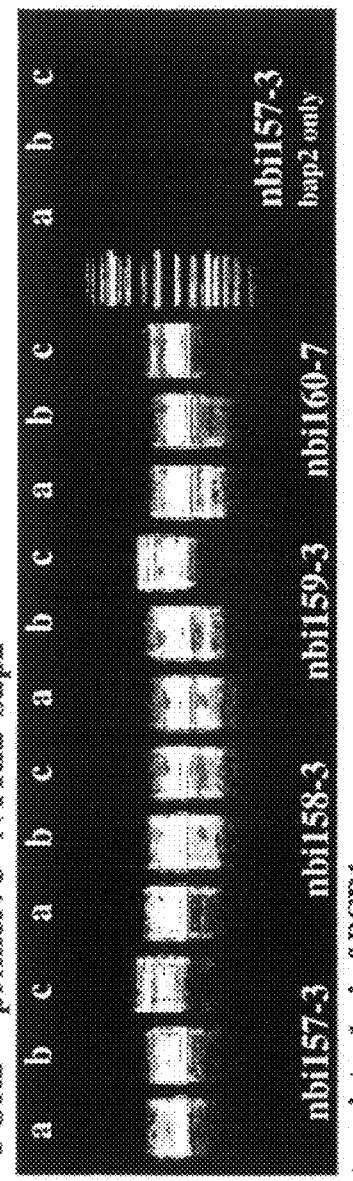
Fig. 13

PROCESS OF CLEAN CLONING

CROSS-REFERENCE TO RELATED APPLICATIONS

This application is the U.S. National Stage of International Application PCT/EP2009/007237, filed Oct. 8, 2009, which designates the U.S. and was published by the International Bureau in English on Apr. 15, 2010, and which claims the benefit of European Patent Application No. 08017649.8, filed Oct. 8, 2008; both of which are hereby incorporated herein in their entirety by reference.

FIELD OF THE INVENTION

The present invention relates to a process of cloning a nucleic acid sequence that may be of unknown nucleotide sequence and that flanks (is adjacent to) a nucleic acid sequence of known nucleotide sequence in genomic DNA or RNA. The invention also relates to a process of inserting a nucleic acid sequence of interest that may be of unknown nucleotide sequence into an acceptor nucleic acid or acceptor vector. The nucleic acid sequence of unknown nucleotide sequence may be sequenced after the insertion or cloning step, e.g. for determining the location of the nucleic acid sequence of known nucleotide sequence in the genome.

BACKGROUND OF THE INVENTION

Since its development, the polymerase chain reaction (PCR) has revolutionized the field of molecular biology. PCR is a process by which any DNA sequence of interest (of reasonable size) located between two known sequences can be amplified using two primers homologous to these two known sequences, one primer being a forward primer and the other primer (binding to the complementary strand) being a reverse primer. PCR allows to easily clone any sequence of interest, provided that two known flanking sequences are available. No knowledge of the sequence located between the two primer binding sites is required.

A related but different problem in molecular biology is the identification of unknown sequences that flank a region of known nucleotide sequence. PCR cannot be used directly to amplify a fragment containing the known and unknown sequence, since the sequence at only one end of the fragment to be amplified is known for primer design. Examples of such problems include the determination of the nucleotide sequence flanking a stably integrated transgene (for example in a T-DNA), the nucleotide sequence flanking a transposon insertion, or the nucleotide sequence of the variable region of an antibody for which only the isotype is known. The first two examples refer to DNA molecules, while the third example refers to RNA molecules. This difference is not important since RNA molecules can be converted to cDNAs by reverse transcription using a primer binding at the known region.

Over the years, many protocols have been developed to provide solutions for the identification of unknown sequences that flank known sequences. Many of these protocols use either attaching an adaptor to the end of the unknown sequence or to use PCR using one or several unspecific primers (primers containing both a known constant sequence, an adaptor sequence, followed by random or unspecific variable sequence) that binds randomly to DNA, including to sequences in the vicinity of the known sequence. Two to three PCRs are then performed using combinations of adaptor primers and known region-specific primers (or gene-specific primers, abbreviated herein by "gsp"). After the first PCR, both specific and non-specific products are typically obtained. The ratio of specific products increases in the second PCR performed using an adaptor primer and a nested known sequence-specific primer, but many unspecific products are still present. Identification of the unknown sequence can be done by sequencing the amplified product. However, if several specific products are expected to be amplified in the same amplification (for example a genome might contain several transgenes or several transposons, or an RNA population might contain a large number of different antibodies), direct sequencing will not be useful. Rather, the amplified product will have to be cloned, and recombinant plasmids individually sequenced.

There are many approaches for cloning of PCR products. Cloning is typically done by ligating together DNA fragments that have been prepared by digestion with type II restriction enzymes. This process usually requires several steps: (1) the plasmids (or PCR products) containing the fragment to be subcloned or the recipient vector are digested with one or two restriction enzymes, (2) the digested fragments are separated using gel electrophoresis, and then the desired fragments extracted from the gel, (3) the purified vector and insert fragments are ligated together using a DNA ligase such as T4 DNA ligase, (4) the ligation is transformed in competent *E. coli* cells.

One limitation of standard cloning techniques is that the restriction sites chosen for cloning must not be present within the fragment to be cloned. Since for the problem discussed here, a part of the sequence to be cloned is not known, it can be expected that using restriction enzymes for cloning will result in the loss of part of the sequence of some of the amplified fragments, or even completely prevent cloning of some of the products.

An entirely different cloning strategy has been developed that does not require restriction enzymes: this strategy relies on generating DNA ends that are single-stranded both on the DNA insert and the vector. Complementary single-stranded overhangs on the DNA insert and in the cloning vector will anneal. If the annealed region is more than 12-15 nucleotides, and the two ends of a linear insert anneal with the two ends of a linearized piasmid vector, ligation-free cloning can be achieved. Host cells such as *E. coli* cells transformed with the annealed product will repair the nicks, leading to the formation of a circular plasmid capable of replicating (Li & Evans, 1997, *Nucleic Acids Res.*, 25, 4165-4166).

One of the first cloning methods that were developed based on this principle was UDG cloning. PCR amplification of a DNA fragment was performed using primers containing an arbitrary 12 nucleotide extension containing at least 4 uracils. The vector was also amplified by PCR using primers containing a 12 nucleotide extension complementary to the extension in the primers for the insert. After PCR amplification, insert and vector were treated with uracil DNA glycosylase, which opens the DNA extensions in the vector and insert (UDG catalyzes the hydrolysis of the N-glycosylic bond between the uracil and sugar), creating single-stranded DNA ends. After annealing vector and insert, the mix was transformed in *E. coli* using chemically competent cells. *E. coli* then trims and repairs the ends at the junction site (Nisson P. E., Rashtchian A., & Watkins P. C., 1991, *PCR Methods Appl.*, 1:120-123).

The advantage of this strategy is that it is efficient and results in very few empty vector constructs. The drawbacks are that (1) primers containing uracil are expensive, (2) the entire vector has to be amplified by PCR, and (3) the extension of primers has to contain 4 uracils and 4 adenines (complementary to the uracils in the extension of the complementary fragment) and therefore cannot consist of any 12 nucleotide sequence of choice.

Another strategy developed even earlier, ligation-independent cloning (LIC), was developed based on the 3' to 5' exonuclease activity of T4 polymerase (Aslanidis C. & de Jong, P. J., 1990, *Nucleic Acids Res.*, 18:6069-6074). As with UDG cloning, a PCR fragment is amplified with two primers that contain 12 nucleotide extensions, these extensions lacking one of the 4 nucleotides, for example G. This amplified fragment is then treated with T4 polymerase in a buffer that contains dGTP but none of the other nucleotides. The 3' to 5' exonuclease activity of T4 polymerase removes all nucleotides until the first G encountered, at which point it stops since an equilibrium is obtained between removal and incorporation of this nucleotide. This treatment therefore creates a 12 nt (nt stands for nucleotide herein) single-stranded extension that can be used for annealing of vector and insert. The vector contains ends that are compatible with the insert and are made by digestion with T4 polymerase in the presence of dCTP.

In a similar work, DNA and insert were treated with T4 polymerase, but without addition of any nucleotide (Yang et al., 1993, *Nucleic Acids Res.*, 21:1889-1893). Since the single-stranded extension might be longer than 12-15 nucleotides, the annealed mix was treated by adding all 4 deoxynucleotides and T4 polymerase to fill the single-stranded gaps.

Another procedure similar to both techniques described above (sequence and ligation-independent cloning: SLIC) is described in US 2007/0292954. The procedure is similar to the work of Yang et al., but gaps in the annealed heteroduplex are not filled with DNA polymerase. This work also describes the assembly of up to 10 fragments in a vector.

These three related strategies allow cloning without using standard restriction sites at the junction sites between vector and insert. However, non-specific amplification products obtained when one of the primers anneals to a random sequence non-specifically or primer dimers can be cloned in addition to the specific products. There is therefore a need for a cleaner cloning strategy.

GENERAL DESCRIPTION OF THE INVENTION

Departing from the prior art, it is a problem of the invention to provide a process of cloning a nucleic acid sequence of interest comprising a sequence segment U of unknown nucleotide sequence and a sequence segment of known sequence into an acceptor nucleic acid such as a cloning vector, whereby cloning of unspecific PCR products is suppressed. This problem is solved by the processes described herein.

Thus, the invention provides:
(1) A process of inserting a nucleic acid sequence of interest into an acceptor nucleic acid, comprising the following steps:
amplifying by PCR a DNA comprising in the following order a sequence segment U, a nucleic acid sequence segment K2 and a nucleic acid sequence segment of known sequence K3 using a forward primer defining a first end of the amplified DNA and a reverse primer defining a second end of the amplified DNA,
treating the linear double-stranded DNA molecules contained in the PCR product obtained in the previous step with an exonuclease to obtain a single-stranded overhang at the first end of the DNA and a single-stranded overhang comprising nucleic acid sequence segments K2 and K3 at the second end of the DNA;
annealing the product of the previous step to a linearized double-stranded acceptor nucleic acid having at a first end thereof a single-stranded overhang having complementarity to the single-stranded overhang of the first end of the DNA and at a second end thereof a single-stranded overhang having complementarity to the single-stranded nucleic acid sequence segment K2 of the second end of the DNA; and
optionally transforming the reaction product obtained in the previous step into a host cell.
(2) The process according to (1), further comprising generating a template for said PCR, comprising attaching a primer binding sequence to a nucleic acid sequence comprising, in the following order, the nucleic acid sequence segment U, a nucleic acid sequence segment of known sequence K2 and a nucleic acid sequence segment of known sequence K3, said forward primer hybridizing to the primer binding sequence.
(3) The process according to (2), wherein the primer binding sequence is a homooligomeric nucleotide sequence segment attached using terminal deoxyribonucleotide transferase.
(4) The process according to (2) or (3), wherein said forward primer comprises an adaptor sequence segment and a sequence segment complementary to the primer binding sequence.
(5) The process according to (1), further comprising generating a template for said PCR, comprising attaching an adaptor sequence to a nucleic acid sequence comprising, in the following order, the nucleic acid sequence segment U at the first end of the nucleic acid sequence, a nucleic acid sequence segment of known sequence K2 and a nucleic acid sequence segment of known sequence K3.
(6) The process according to any one of (1) to (5), wherein said acceptor nucleic acid does not contain a sequence portion complementary to single-stranded sequence segment K3 in the single-stranded overhang at the second end of the acceptor nucleic acid.
(7) The process according to any one of (1) to (6), wherein the exonuclease is a 3'-5'-exonuclease. Examples for the exonuclease are *E. coli* T4 DNA polymerase, the large fragment of *E. coli* polymerase I large fragment (Klenow polymerase), lambda nuclease, 17 nuclease or exonuclease Ill, preferably it is *E. coli* T4 DNA polymerase.
(8) The process according to any one of (1) to (7), wherein said host cell is a bacterial cell such as *E. coli* or *Agrobacterium tumefaciens*.
(9) The process according to any one of (1) to (8), wherein a pre-amplification step is performed by PCR before said PCR reaction defined in claim 1, using a forward primer defining the first end of the PCR product of the pre-amplification step and a reverse primer terminating at its 3'-end in a nucleotide sequence of nucleic acid sequence segment K3.
(10) The process according to (2) or (5), wherein the attaching step is performed in a mixture comprising genomic DNA isolated from eukaryotic prokaryotic cells.
(11) The process according to (2) or (5), wherein said attaching step is performed at the 3'-end of a cDNA retro-transcribed from an mRNA.
(12) The process according to any of (1) to (11), wherein the acceptor nucleic acid does not contain a sequence segment of more than 10 nt having homology to segment K3 within a range rendered single-stranded at the second end of the acceptor nucleic acid, such as within a region of 100 nt from the second end of the acceptor nucleic acid.

(13) A process of inserting a nucleic acid sequence of interest comprising a nucleic acid sequence segment U of unknown nucleotide sequence into an acceptor nucleic acid, comprising the following steps:
  attaching a primer binding sequence to a nucleic acid sequence comprising, in the following order, the nucleic acid sequence segment U at the first end of the nucleic acid sequence, a nucleic acid sequence segment of known sequence K2 and a nucleic acid sequence segment of known sequence K3;
  amplifying by PCR a DNA comprising in the following order the nucleic acid sequence segment U, nucleic acid sequence segment K2 and nucleic acid sequence segment K3 using a forward primer hybridizing to the primer binding sequence and defining a first end of the amplified DNA, and a reverse primer defining a second end of the amplified DNA, said reverse primer terminating at its 3'-end in a nucleotide sequence of sequence segment K3;
  treating the linear double-stranded DNA molecules contained in the PCR product obtained in the previous step with an exonuclease to obtain a single-stranded overhang at the first end of the DNA and a single-stranded overhang comprising nucleic acid sequence segments K2 and K3 at the second end of the DNA;
  annealing the product of the previous step to a linearized double-stranded acceptor nucleic acid having at a first end thereof a single-stranded overhang having complementarity to the single-stranded overhang of the first end of the DNA and at a second end thereof a single-stranded overhang having complementarity to the single-stranded nucleic acid sequence segment K2 of the second end of the DNA; and
  transforming the reaction product obtained in the previous step into a host cell.

(14) A process of inserting a nucleic acid sequence of interest comprising a nucleic acid sequence segment U of unknown nucleotide sequence into an acceptor nucleic acid, comprising the following steps:
  attaching an adaptor sequence to a nucleic acid sequence comprising, in the following order, the nucleic acid sequence segment U at the first end of the nucleic acid sequence, a nucleic acid sequence segment of known sequence K2 and a nucleic acid sequence segment of known sequence K3;
  amplifying by PCR a DNA comprising in the following order an adaptor sequence, the nucleic acid sequence segment U, nucleic acid sequence segment K2 and nucleic acid sequence segment K3 using a forward primer defining a first end of the amplified DNA and a reverse primer defining a second end of the amplified DNA, said reverse primer terminating at its 3'-end in a nucleotide sequence of sequence segment K3;
  treating the linear double-stranded DNA molecules contained in the PCR product obtained in the previous step with an exonuclease to obtain a single-stranded overhang comprising the adaptor sequence at the first end of the DNA and a single-stranded overhang comprising nucleic acid sequence segments K2 and K3 at the second end of the DNA;
  annealing the product of the previous step to a linearized double-stranded acceptor nucleic acid having at a first end thereof a single-stranded overhang having complementarity to the single-stranded overhang of the first end of the DNA and at a second end thereof a single-stranded overhang having complementarity to the single-stranded nucleic acid sequence segment K2 of the second end of the DNA; and
  transforming the reaction product obtained in the previous step into a host cell.

(15) A process of inserting a cDNA of an RNA sequence of interest into an acceptor nucleic acid, comprising the following steps:
  isolating RNA from a cell;
  retro-transcribing RNA to form a cDNA non-coding strand;
  amplifying by PCR a DNA comprising in the following order a sequence segment U, a nucleic acid sequence segment of known sequence K2 and a nucleic acid sequence segment of known sequence K3 using a forward primer defining a first end of the amplified DNA and a reverse primer defining a second end of the amplified DNA, said reverse primer terminating at its 3'-end in a nucleotide sequence of sequence segment K3;
  treating the linear double-stranded DNA molecules contained in the PCR product obtained in the previous step with an exonuclease to obtain a single-stranded overhang at the first end of the DNA and a single-stranded overhang comprising nucleic acid sequence segments K2 and K3 at the second end of the DNA;
  annealing the product of the previous step to a linearized double-stranded acceptor nucleic acid having at a first end thereof a single-stranded overhang having complementarity to the single-stranded overhang of the first end of the DNA and at a second end thereof a single-stranded overhang having complementarity to the single-stranded nucleic acid sequence segment K2 of the second end of the DNA; and
  transforming the reaction product obtained in the previous step into a host cell.

(16) The process according to any one of (1) to (14), wherein the sequence of interest comprises in 5' to 3'-direction a sequence segment U and a sequence segment K2 of known nucleotide sequence.

(17) The process according to (14), comprising providing a template for said PCR by attaching a primer binding sequence to the 3'-end of said cDNA, wherein the forward primer used in said PCR hybridizes to said primer binding sequence.

(18) The process according to (14), wherein the RNA is mRNA.

(19) The process according to (14), wherein the RNA encodes an immunoglobulin chain, sequence U is part of a variable region of the immunoglobulin, and the known sequences K2 and K3 are part of a constant region of the immunoglobulin.

(20) The process according to any one of (1) to (19), wherein said nucleic acid sequence segment K3 of said amplified DNA has the nucleotide sequence of said reverse primer.

(21) The process according to any one of (1) to (20), wherein said acceptor nucleic acid does not contain a sequence portion of more than 7, preferably of not more than 5, most preferably of not more than 3 contiguous nucleotides complementary to single-stranded sequence segment K3 in terms of standard A-T and G-C base pairing in the single-stranded overhang at the second end of the acceptor nucleic acid.

In the present invention, PCR products are cloned based on homology between sequences present in both the acceptor nucleic acid (that may be an acceptor or cloning vector) and the amplified DNA (insert). Single-stranded overhangs present in the amplified DNA and in the acceptor nucleic acid are complementary and can anneal. The processes of the invention allow cloning of a PCR product containing regions of known (regions K) and a region of unknown (U) nucleotide sequence very efficiently, with a very low amount of religated empty vector; more importantly, unwanted products such as primer dimers are not cloned to any significant extent. In prior art processes of inserting nucleic acids comprising an unknown and a known nucleotide sequence segment, specificity for cloning the desired product is exclusively determined by the use of a PCR primer on the side of the nucleic acid having the known nucleotide sequence. Any unspecific binding of the primer may, in the prior art, amplify undesired DNA sequences that will be inserted into the acceptor nucleic acid (or cloning vector), since annealing to the acceptor nucleic acid is determined by the nucleotide sequence introduced into the PCR product by the primer. In contrast, two measures are taken for achieving specificity in cloning a nucleic acid sequence of interest in the present invention. First, primer binding to a known sequence segment of the template used in the PCR step is used in the amplification step before annealing. The reverse primer defining the second end of the amplified DNA binds to a known sequence of the PCR template corresponding to sequence segment K3. Second, a sequence segment of the known sequence (K2) different from the sequence segment used for primer binding (K3) is used for annealing the PCR product with the acceptor vector. Since unspecific PCR product nucleic acids obtained by unspecific primer binding will generally not contain sequence segment K2 used for hybridization with the acceptor nucleic acid (or acceptor vector), such unspecific PCR product nucleic acids are not inserted into the acceptor vector to a significant extent. Further, primer dimers are not inserted into the acceptor vector (FIG. 1b). The processes of the invention have an extraordinary high efficiency for cloning nucleic acids of interest. These two measures are achieved in the invention by a suitable choice of the primer binding region used in the PCR step and a suitable choice of the sequence region of the PCR product used for homology cloning with the acceptor vector. Interestingly, the specificity of this cloning strategy allows 'cleaning' of the PCR product, even when using product from the first PCR amplification step using genomic DNA as template or total RNA isolated from cells. Although the product of the first PCR amplification may be a mixture of specific and non-specific amplification products, specific products are inserted essentially exclusively into the acceptor vector. The fact that specific products are cloned essentially exclusively allows sequencing plasmids from colonies grown from transformed host cells without a pre-screening step, and thus a convenient determination of the nucleotide sequence of segment U is achieved.

BRIEF DESCRIPTION OF THE FIGURES

FIG. 8: Shown are the positions of catching sequences (K2 sequence segments) and amplification primers Mu2N and Mu3N used in human IgM (immunoglobulin Mu chain) constant sequences. Catching sequences for cloning into acceptor nucleic acids ("clean cloning vectors") pICH36101 and pICH36113, as well as primer binding sequences of reverse primers Mu2N and Mu3N, respectively, are indicated. The nucleotide sequence shown is referred to herein as SEQ ID NO: 3.

FIG. 9: Shown are the positions of catching sequences and amplification primers used in human IgK (immunoglobulin kappa chain) constant sequences. Catching sequences for cloning into acceptor nucleic acids ("clean cloning vectors") pICH36078 and pICH36083, as well as primer binding sequences of reverse primers KC2N and KC3N, respectively, are indicated. The nucleotide sequence shown is referred to herein as SEQ ID NO: 4.

FIG. 10: Test of T4 exonuclease activity at different temperatures and nucleotide concentrations. L: GeneRuler 1 kb DNA Ladder Plus (Fermentas).
Reaction Conditions:
DNA: pICH10990 SacII/NdeI digested (10 μl/50 μl), (Fragment sizes: 3595, 1563, 1158, 125 bp) 2.5 μl/10 μl used for T4-Pol. treatment
T4-Pol.: 0.5 μl/10 μl=1.5 U/10 μl in 2 NEB+BSA Incubation: 10 min at 25° C., 20° C., 15° C. or 10° C., all heat inactivated: 5 min 80° C.;
C=control without T4; H=heat inactivation control (after addition of T4-Pol. 5 min 80° C.).
Mung Bean Nuclease treatment: addition of 1.5 μl Mung Bean Nuclease buffer, 1 μl Mung Bean nuclease (10 U/μl), ad 15 μl H$_2$O, 20 min 25° C.

FIG. 11: T4 clean cloning: test of different T4 polymerase digestion times at room temperature.

FIG. 13: Flanking sequences PCR (F-PCR) on *Nicotiana benthamiana* plants transgenic for construct pICH30649.

Figure 1A:
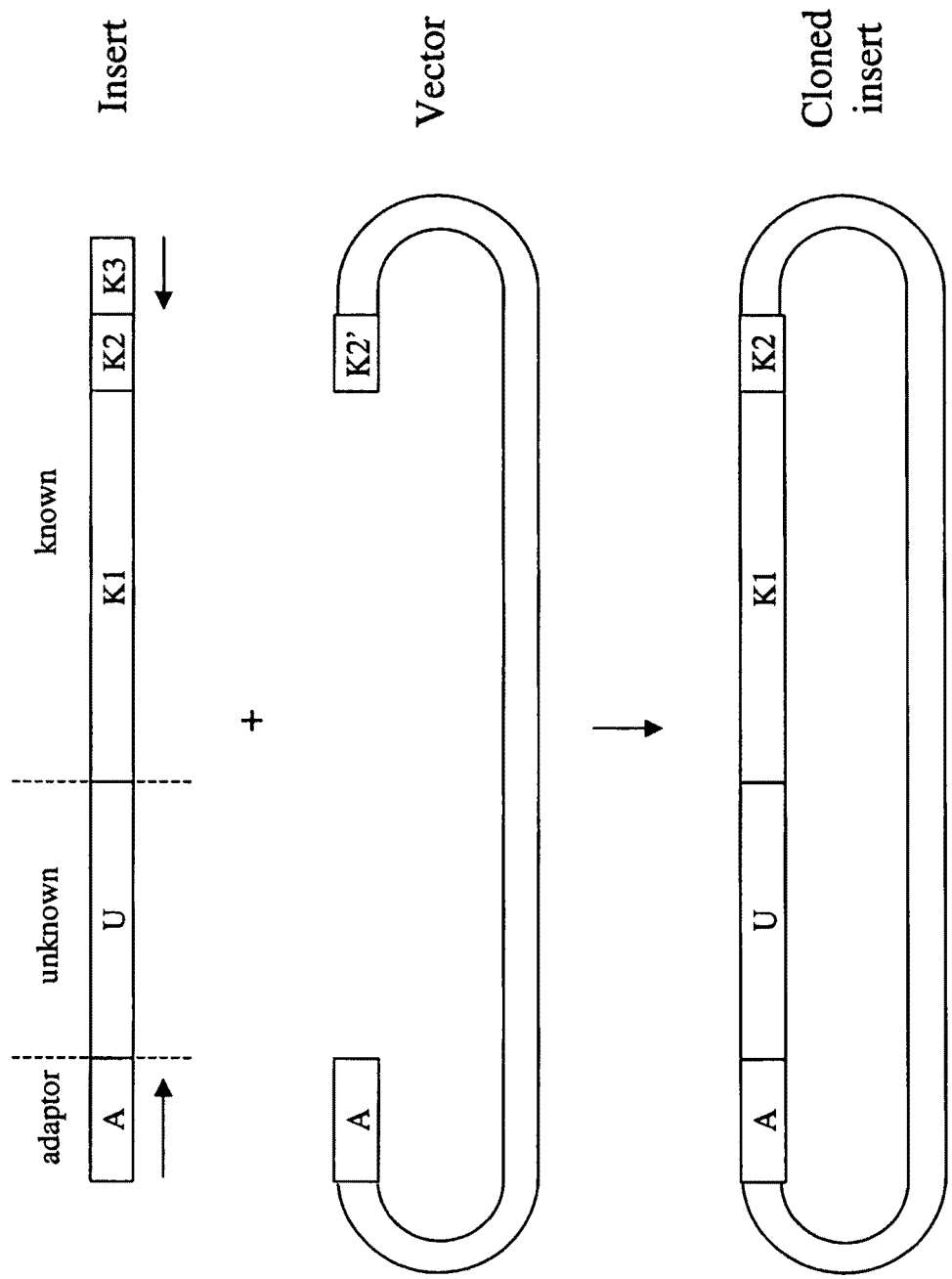
FIG. 1: Principle of the clean cloning strategy. An insert to be cloned is amplified by PCR with a primer with homology to the target (region K3) and a primer homologous to an adaptor sequence (A) added at the end of the region of unknown sequence (U) (FIG. a). The fragment is cloned by homology into a vector containing sequences (A) and (K2). Since sequence K2 is not present in the primers used for amplification, unspecific products and primer dimers cannot be cloned (FIG. 1b). A' and K3' are sequences derived from A and K3, respectively.
Figure 1B:
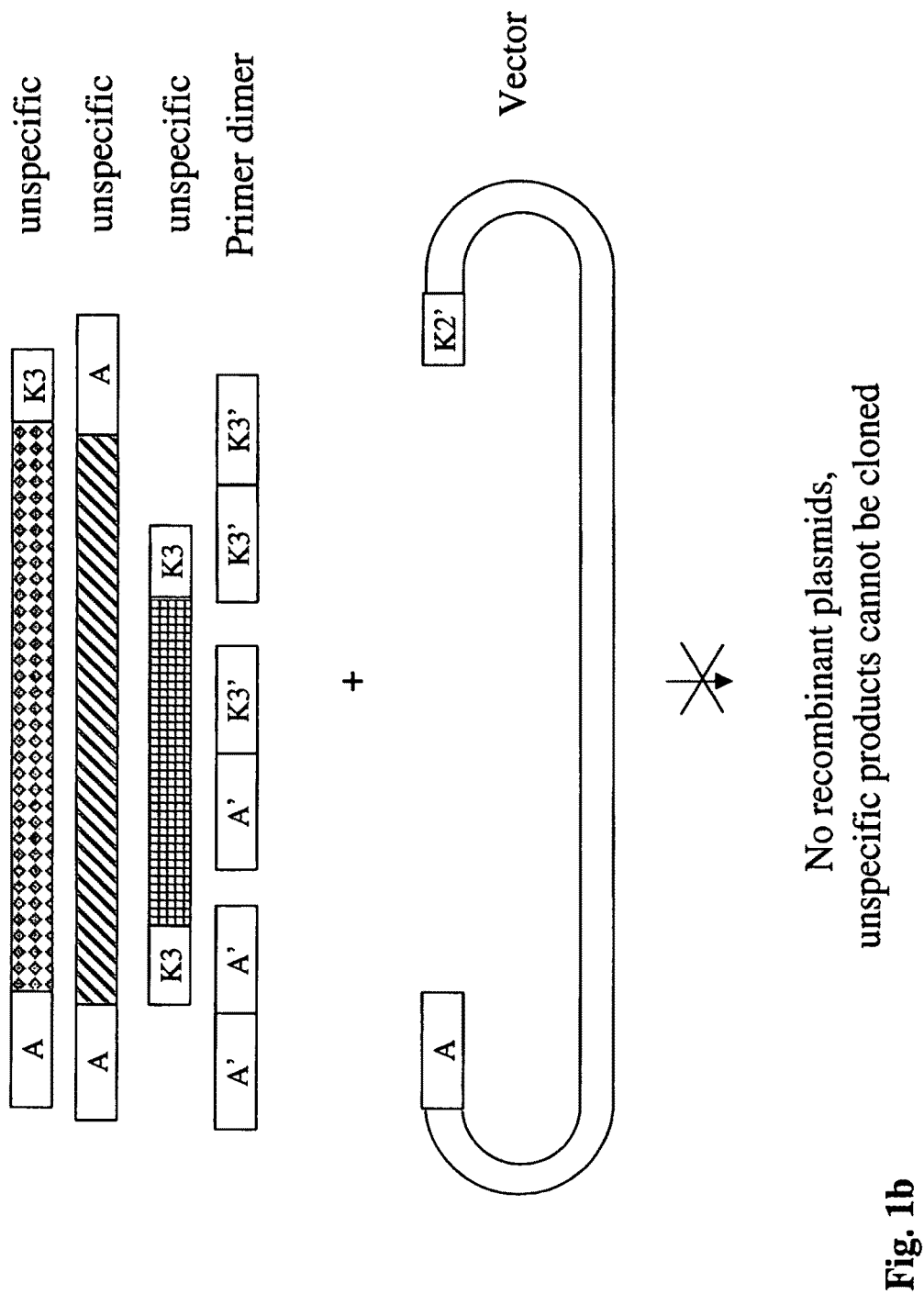

KLENOW TREATMENT 2.5 μl/10 μl pICH10990 SacII/NdeI digested (10 μl/50 μl), (Fragment sizes: 3595, 1563, 1158, 125 bp)
1 μl/10 μl=10 U/10 μl Klenow in 2 NEB+BSA
30, 60, 90, 120 min at 37° C. or Room temperature (25° C.), all heat inactivated: 5 min 80° C.;
0 min=control without T4;
Mung Bean Nuclease Treatment:
+1.5 μl Mung Bean Nuclease buffer, 1 μl Mung Bean nuclease (10 U/μl), ad 15 μl H2O, 20 min 25° C.

Klenow Cloning:
1 μl/10 μl vector=pICH31401 PstI, 0.5 μl insert=PCR on pICH3491x (*Arabidopsis* library) ecolib3+4,
0.5 μl=2.5 U/10 μl Klenow,
30, 60, 120 min 37° C., 5 min 80° C.
All 10 μl transformed in chemical competent DH10B cells, 500 μl LB added, 25 μl plated on LB with Garb and X-Gal after 15 min shaking at 37° C.

DETAILED DESCRIPTION OF THE INVENTION

The nucleic acid sequence of interest to be cloned or to be inserted into an acceptor nucleic acid may be DNA or RNA. If it is RNA, it is cloned after reverse-transcription to cDNA. The acceptor nucleic acid is generally double-stranded DNA. Thus, cloning an RNA sequence of interest means cloning a cDNA of the RNA sequence of interest. Cloning of a nucleic acid sequence of interest herein means inserting the nucleic acid sequence of interest into an acceptor nucleic acid. The nucleic acid sequence of interest may be inserted into the acceptor nucleic acid as part of a larger nucleic acid molecule that contains, in addition to the nucleic acid sequence of interest, an adaptor sequence and a segment K2 that are used for homology cloning. Homology cloning herein means inserting a nucleic acid sequence of interest into an acceptor nucleic acid, whereby both the nucleic acid sequence of interest and the acceptor nucleic acid are provided with single-stranded overhangs and whereby single-stranded overhangs on both sides of the nucleic acid sequence of interest anneal to single-stranded overhangs of the linearized acceptor nucleic acid by base-pairing. Cloning may further comprise transforming the acceptor nucleic acid having integrated the nucleic acid of interest into a suitable host cell. Cloning may further comprise growing separate clones from the transformed host cells.

The acceptor nucleic acid is generally a cloning vector. The terms "cloning vector" and "acceptor nucleic acid" mean a double-stranded DNA molecule that can be maintained in suitable host cells. The acceptor nucleic acid may have an origin of replication for enabling replication in the host cells employed. Further or additionally, the acceptor nucleic acid (or cloning vector) may have a selectable marker allowing selection of suitable host cells containing the acceptor nucleic acid.

The processes of the invention has its main application in the cloning, determination and identification of unknown nucleic acid sequences that flank a nucleic acid sequence of known nucleotide sequence. The concept of the present invention does, however, not require that a nucleic acid sequence of interest to be cloned has a nucleic acid sequence segment of unknown nucleotide sequence at one end. If the nucleotide sequence at both ends of the nucleic acid of interest to be cloned is known, the steps of attaching a primer binding sequence or an adaptor sequence can be omitted, and both the forward and the reverse primer used in the PCR step can be designed to bind specifically for PCR purposes to both ends of the nucleic acid of interest present in the PCR template. In any event, after having attached a primer binding sequence or an adaptor sequence to a nucleic acid sequence segment U of unknown sequence present in a nucleic acid sequence of interest, the obtained nucleic acid sequence will contain at both ends sequence segments of known nucleotide sequence that can be used for primer binding in the PCR step of the invention.

Generally, the nucleic acid sequence of interest comprises sequence segment U that may be of unknown nucleotide sequence. The nucleic acid sequence of interest may further comprise a nucleic acid sequence segment (briefly "segment") of known nucleotide sequence such as segment K2 or a part thereof. Segment K2 is used for inserting a nucleic acid of interest into the acceptor nucleic acid by base pairing between single-stranded segment K2 and a complementary single-stranded segment of the acceptor vector referred to as K2'. Segment K2 is also referred to herein as "catching sequence", since it is caught by segment K2' of the acceptor nucleic acid. Segment K3 has the nucleotide sequence of the reverse primer used in the PCR amplification step of the invention and defines segment K3 in the amplified DNA. A sequence segment in the PCR template used in the PCR step that is homologous to the reverse primer, such that annealing of complementary strands of reverse primer and template is achieved in the PCR step, may also be referred to as segment K3. Segment K3 is not inserted into the acceptor nucleic acid and is therefore not part of the nucleic acid sequence of interest. Thus, the sequence of interest that is inserted into the acceptor nucleic acid comprises in 5' to 3'-direction a sequence segment U and a sequence segment K2 of known nucleotide sequence, and does not comprise sequence segment K3 of the reverse primer. Preferably, the sequence of interest does not contain more than 10, preferably not more than 6, more preferably not more than 3 contiguous nucleotides of sequence segment K3 that are inserted into the acceptor nucleic acid.

Figure 2:
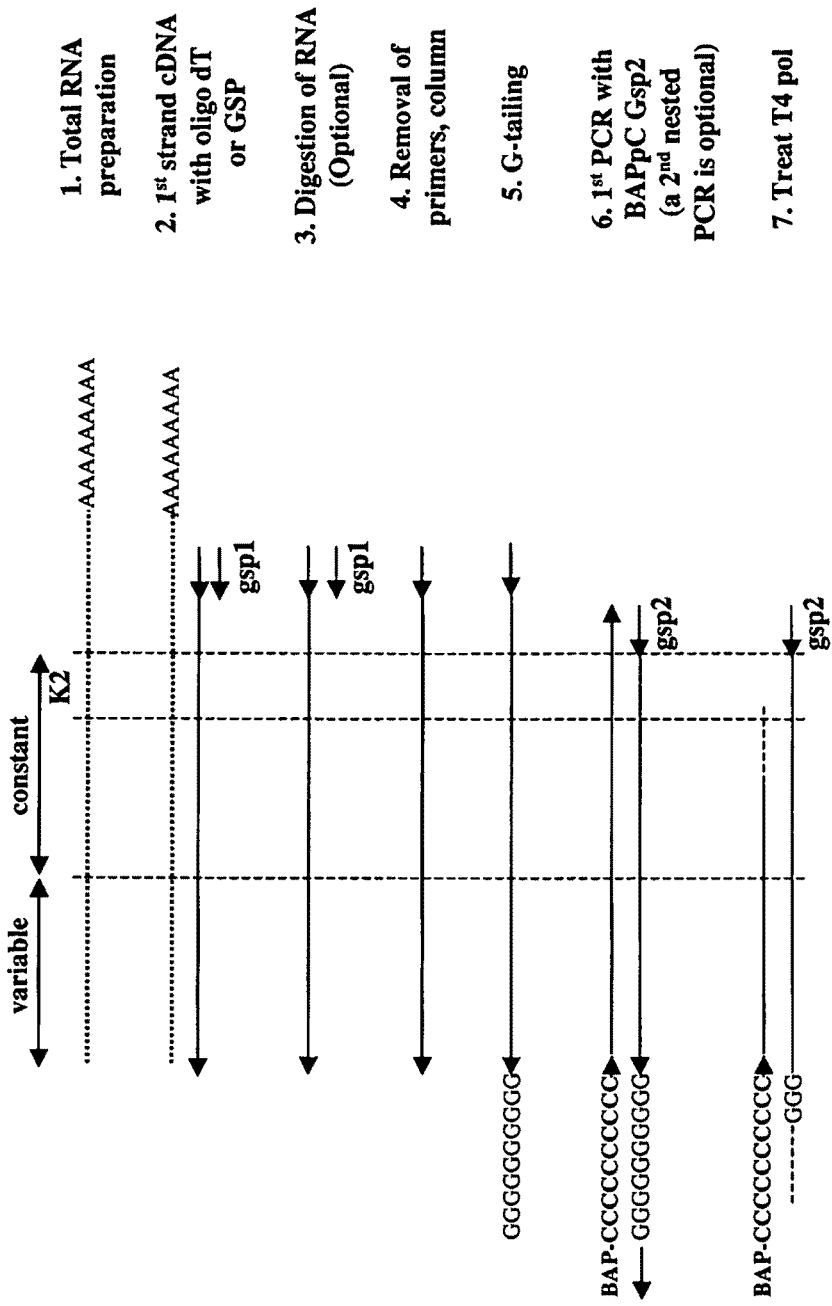
FIG. 2: Cloning of flanking sequences from a RNA template: preparation of insert for clean cloning. gsp: gene-specific primer; BAPpC: primer used for PCR containing an adaptor sequence referred to as "BAP" and a 3' tail of cytosine nucleotides. The oligo-G sequence shown is SEQ ID NO: 1. BAP-CCCCCCCCCC is SEQ ID NO: 9. The region referred to as "variable" is a sequence segment the nucleotide sequence of which may be unknown (also referred to herein as sequence segment U), such as a variable sequence of an antibody. The region referred to as "constant" is a sequence segment K of known nucleotide sequence comprising sequence segment K2. However, polymorphisms may occur in the constant region in samples from different patients. The constant sequence region may be the constant sequence of an antibody. Sequence segment K2 is not used as a primer binding region for PCR, but can be used for homology cloning into an acceptor nucleic acid. On the right hand side of sequence segment K2, sequence segment K3 is shown that is used for primer binding and PCR amplification. If a second nested PCR is performed in step 6, the first PCR is considered a pre-amplification. In general, however, no pre-amplification is required for achieving sufficient amounts of specific product in the strategy shown in FIG. 2.

Herein, the end of a segment U-containing nucleic acid sequence closer to sequence segment U is referred to herein as "first end" of the respective nucleic acid. The other end of a nucleic acid that is closer to nucleic acid sequence segment K2 is referred to as "second end" of the respective nucleic acid. Similarly as depicted in FIG. 2 for segment K2, the nomenclature of segments U, K1 and/or K3 can be applied not only to the amplified DNA but also to the PCR template, the corresponding genomic DNA, corresponding RNA or a cDNA corresponding to the RNA.

The process of the invention comprises a step of amplifying by PCR a DNA comprising in the following order a sequence segment U, a nucleic acid sequence segment of known sequence K2 and a nucleic acid sequence segment of known sequence K3 using a forward primer defining a first end of the DNA and a reverse primer defining a second end of the DNA. The DNA recited in this process step is the DNA amplified in this step. Thus, this DNA is also referred to herein as "amplified DNA". The reverse primer terminates at its 3'-end in a nucleotide sequence of nucleic acid sequence segment K3. Preferably, the reverse primer determines sequence segment K3 of the amplified DNA, i.e. sequence segment K3 consists of the nucleotide sequence of the reverse primer and, in double stranded amplified DNA, the complementary sequence of the nucleotide sequence of the reverse primer. Thus, segment K3 on the PCR template is the region chosen as the primer binding region of the reverse primer.

The amplified DNA terminates at its first end by the nucleotide sequence determined by the forward primer, and terminates at its second end by the nucleotide sequence determined by the reverse primer. Apart from segments U, K2 and K3, the DNA may further have other sequence portions present in the template used for PCR such as a further nucleic acid sequence segment K1 in between segments U and K2. Segment K1 may be of known nucleotide sequence. Segments K2 and K3 do not need to be contiguous. Instead, segments K2 and K3 may be separated by another sequence segment. In general, however, segments K2 and K3 are not separated by more than 100 nt ("nt" stands for nucleotides). Preferably, however, segments K2 and K3 are contiguous. If the nucleotide sequence of segment U is not known, the amplified DNA may further contain at its first end an adaptor sequence used for annealing the first end of the DNA to the first end of the acceptor nucleic acid in the annealing step.

Segment K2 is defined as a nucleic acid segment homologous to sequence segment K2' present at the second end of the linearized acceptor nucleic acid for allowing annealing of the single-stranded second end of the amplified DNA to the single-stranded second end of the acceptor nucleic acid by base pairing between complementary strands. The length of segment K2 and the degree of homology to segment K2' should be such that stable annealing can be achieved in the annealing step. For this purpose, the length of segment K2 is at least 10 and should be at least 12 nucleotides, better at least 16 nucleotides, even better at least 20 nucleotides, and preferably at least 25 nucleotides. There is no strict upper limit for the length of segment K2. For convenience, it will generally be at most 100 nt. When comparing the degree of homology between segments K2 and K2', sequence segments (or "blocks") of identical length in terms of the number of nucleotides are compared. The degree of homology between segment K2 and segment K2' should be as high as possible for ensuring specific annealing. For example, segments K2 and K2' should contain a block of at least 10 contiguous nucleotides of identical nucleotide sequence. However, the block of identical nucleotide sequences in segments K2 and K2' may be longer than 10 nt, such as at least 12, at least 15 or at least 20 contiguous nucleotides. The higher the homology between segments K2 and K2', the better can unknown polymorphisms that may occur in segments K2 derived from samples from different individuals or patients be tolerated without preventing successful cloning. The relation between annealing tendency of complementary DNA strands and similarity of the strands belongs to the general knowledge of the person skilled in the art so that it is always easy for the skilled person to design a suitable segment K2' dependent from a given segment K2. If, herein, the nucleotide sequence of segment K2 is referred to as being of known nucleotide sequence, this does not mean that the nucleotide sequence must be known exactly. Instead, it is sufficient that sequence segment K2 anneals in the annealing step to sequence segment K2' that is engineered such that complementary strands of segments K2 and K2' can anneal in the annealing step of the invention.

Segment K3 is defined as the nucleic acid sequence segment introduced into the amplified DNA in the PCR step by the reverse primer (and the complementary sequence of the reverse primer produced in said PCR). Regarding the length and nucleotide sequence to be employed for the reverse primer, considerations apply as are generally applied in PCR by the skilled person. Generally, the reverse primer has a length of between 10 and 50 nt or between 14 and 30 nt. The nucleotide sequence of the reverse primer and thus of segment K3 are chosen such that suitable binding to the template used in the PCR is achieved.

Herein, segments K2 and K3 are separate segments that do not overlap to a significant extent. Preferably, they do not overlap by more than 3 nt or not more than by 1 nt. This means that separate segments are used for PCR amplification on the one hand and for insertion into the acceptor nucleic acid on the other hand at the second end of both the DNA and the acceptor nucleic acid. Lack of overlap between segments K2 and K3 may be achieved by designing the reverse primer such that it terminates at its 3'-end in a nucleotide sequence of nucleic acid sequence segment K3. In other words, the reverse primer should not extend with its 3'-end into segment K2 that has homology to a nucleotide sequence segment K2' present at the second end of the acceptor nucleic acid.

In order to prevent that the amplified DNA hybridizes with single-stranded segment K3 to the single-stranded second end of the acceptor nucleic acid in the annealing step, segments K2 and K3 must be sufficiently different, i.e. lack significant homology. The skilled person can judge from general knowledge when two nucleotide sequences are sufficiently different to prevent annealing of complementary strands. A lack of significant homology may mean that K2 and K3 do not contain a block of 9 or more contiguous nucleotides of identical nucleotide sequences, and preferentially do not contain a block of 5 or more contiguous nucleotides of identical nucleotide sequences. Similar considerations apply to the nucleotide sequence of the adaptor A and of segment K2.

In order to prevent that the amplified DNA hybridizes with single-stranded segment K3 to the single-stranded second end of the acceptor nucleic acid in the annealing step, the single-stranded overhang at the second end of the linearized double-stranded acceptor nucleic acid does not contain a sequence portion of more than 7, preferably of not more than 5, most preferably of not more than 3 contiguous nucleotides complementary to single-stranded sequence segment K3 of the second end of the amplified DNA. Herein, complementary means preferably that only standard A-T and G-C base pairing is allowed. Thus, the single-stranded overhang at the second end of the linearized double-stranded acceptor nucleic acid does, in one embodiment, not contain a sequence portion of more than 7, preferably of not more than 5, most preferably of not more than 3 contiguous nucleotides allowing standard A-T or G-C base pairing to single-stranded sequence segment K3 of the second end of the amplified DNA in terms of standard.

After said PCR amplifying step, the DNA molecules contained in the PCR product are treated with an exonuclease to obtain a single-stranded overhang at the first end of the DNA and a single-stranded overhang comprising nucleic acid segments K2 and K3 at the second end of the DNA. If desired, the DNA molecules of the PCR product may be separated from other components of the PCR by methods generally known before exonuclease treatment. The exonuclease may be a 5'-3'-exonuclease or a 3'-5'-exonuclease. Enzymes having exonuclease activity are known in the art. Examples are those used in US 2007/0292954. Examples are the *E. coli* T4 DNA polymerase, the large fragment of *E. coil* polymerase known as Klenow polymerase, lambda nuclease, T7 nuclease or exonuclease III, preferably it is *E. coli* Klenow polymerase. It is not necessary to add dNTPs to the reaction mixture, which gives more flexibility to the process of the invention. Since exonuclease activity of different enzymes having exonuclease activity differs, it is recommended to establish suitable conditions for exonuclease treatment such as temperature, exonuclease concentration and duration of treatment so that a suitable number of nucleotides is removed from the DNA, and overhangs of suitable length are obtained at both ends. A suitable length at the first end and the second end of the amplified DNA is a length that completely exposes those sequence portions required for annealing with the acceptor nucleic acid. At the second end, all of segment K3 and essentially all of segment K2 should be rendered single-stranded. Suitable conditions for T4 DNA polymerase are given in the examples. Also described in the examples is a method for identifying suitable conditions for exonuclease treatment (example 3). Analogous methods may be applied for identifying suitable conditions for other enzymes having exonuclease activity. Although it is possible to perform the exonuclease treatment step with a mixture of two or more exonucleases, a 5'-3'-exonuclease and a 3'-5'-exonuclease should not be combined, since the desired overhangs may not be obtained in this case. After the pre-determined reaction time, exonuclease activity may be destroyed by known methods such as by heating.

Figure 3:
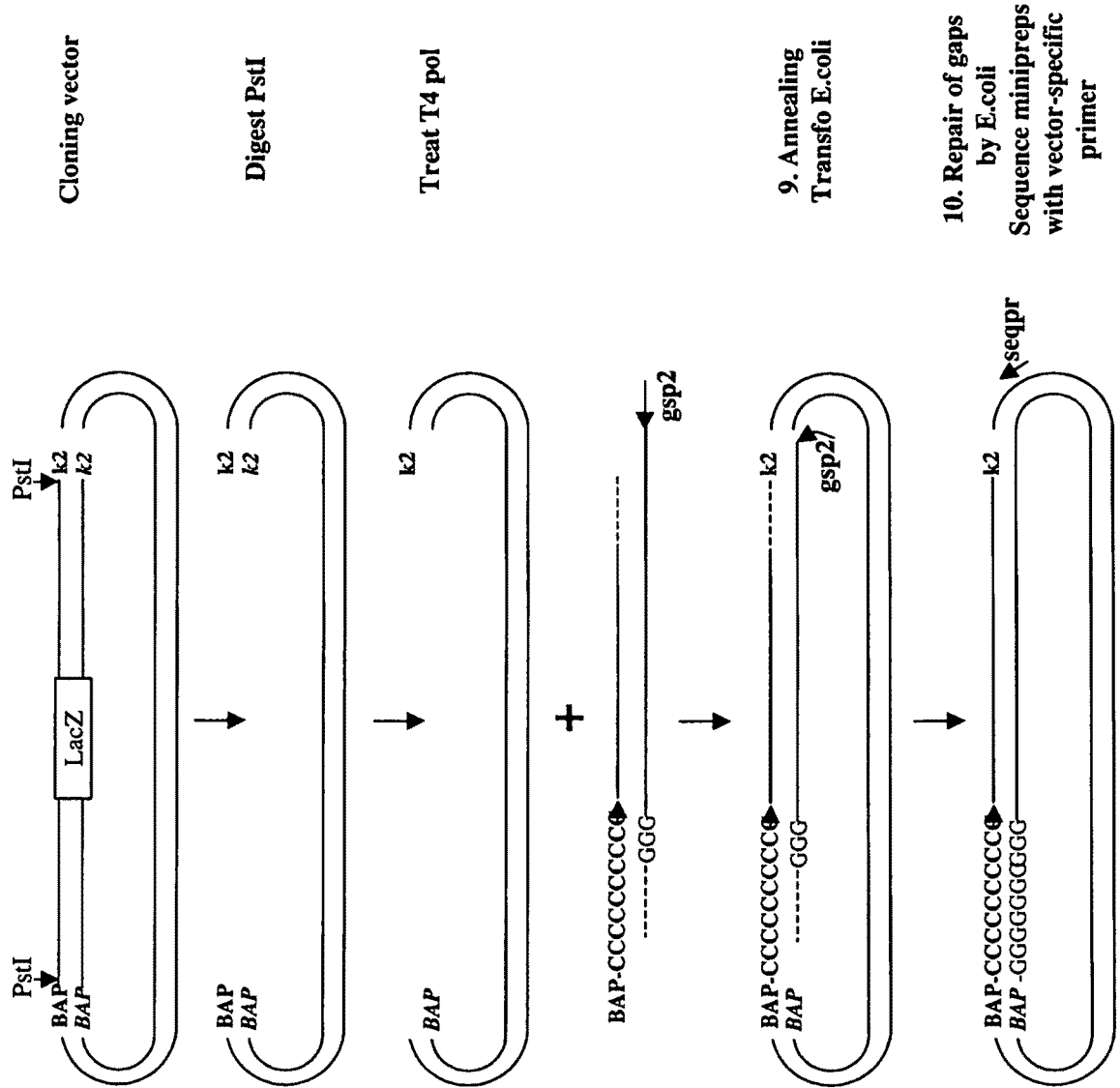
FIG. 3: Preparation of vector for clean cloning and clean cloning of an insert. The cloning vector shown here contains a LacZ gene for blue-white selection. A vector that does not contain LacZ can also be used. The vector is linearized using a restriction enzyme such as PstI. After annealing, the vector is transformed into a host cells such as E. coli. After cloning, the insert can be sequenced using a vector specific primer seqpr.

The acceptor nucleic acid used in the present invention is a linearized double-stranded DNA such as a cloning vector. The acceptor nucleic acid may be created by linearizing a double-stranded acceptor nucleic acid comprising, in the following order, a sequence segment homologous to the first end of the amplified DNA, a vector backbone sequence segment comprising a selectable marker, and a sequence segment K2' that is homologous to sequence segment K2. In one embodiment, the acceptor nucleic acid may be created by linearizing a circular molecule that comprises, in the following order, a first restriction endonuclease cleavage site, the sequence segment homologous to the adaptor sequence segment at the first end of the amplified DNA, the vector backbone sequence segment comprising a selectable marker, the sequence segment K2' homologous to sequence segment K2, and optionally a second restriction endonuclease cleavage site and a spacer sequence segment removable from the acceptor nucleic acid by restriction at said first and at said second restriction endonuclease cleavage site. The spacer sequence segment may contain IacZ for blue/white selection of clones obtained after transforming the reaction product form the annealing step into host cells, cf. FIG. 3.

Linearization can be achieved by treatment with a restriction endonuclease recognizing the first or/and the second restriction endonuclease cleavage site. It is possible and preferred that linearization is performed in the same reaction mixture wherein exonuclease treatment of the amplified DNA and of the linearized acceptor nucleic acid is performed.

The acceptor nucleic acid thus contains at its first end a sequence segment homologous to a sequence segment at the first end of the amplified DNA. If segment U is of unknown nucleotide sequence, the first end of the amplified DNA will be formed by an adaptor sequence A added to the first end of the amplified DNA in said PCR or in a preceding step (see further below). At its second end, the acceptor nucleic acid contains segment K2' that is homologous to segment K2 of the amplified DNA so that complementary strands of segment K2' and segment K2 can anneal. "Complementary" thus does not mean that exclusively G-C and A-T base pairs are formed upon annealing. Instead, some mis-pairing is tolerated provided that stable annealing can be achieved (see above regarding the degree of homology between segments K2 and K2'). Segments K2 and K2' are preferably of similar or identical length. It is possible that a sequence segment of any nucleotide sequence is present between the second end of the acceptor nucleic acid and segment K2'. If present, such sequence segment is shorter than 50 nt, preferably shorter than 20 nt. In one embodiment, the second end coincides with segment K2'. The acceptor nucleic acid does not contain a sequence block of more than 9, preferably of more than 5, contiguous nucleotides that is also present with identical nucleotide sequence in segment K3 within a range rendered single-stranded in the exonuclease treatment step of the acceptor nucleic acid, such as within a region of 100 nt from the second end of the acceptor nucleic acid.

Before the annealing step, the linearized double-stranded acceptor nucleic acid is provided at both ends with single-stranded overhangs required for the annealing step. The single-stranded overhangs may be obtained by exonuclease treatment similarly as described above for the amplified DNA. If a 5'-3'-exonuclease is used for the amplified DNA, a 5'-3'-exonuclease is also used for the acceptor nucleic acid. If a 3'-5'-exonuclease is used for the amplified DNA, a 3'-5'-exonuclease is also used for the acceptor nucleic acid. In one embodiment, the exonuclease treatment of the amplified DNA and of the acceptor nucleic acid is done in the same reaction vessel, i.e. as a one-pot reaction.

The annealing step of the invention is performed by incubating the exonuclease-treated amplified DNA with the linearized double-stranded acceptor nucleic acid having at a first end thereof a single-stranded overhang complementary to the single-stranded overhang of the first end of the DNA and at a second end thereof a single-stranded overhang complementary to the single-stranded sequence segment K2 of the second end of the DNA. Incubation is carried under conditions allowing said annealing.

After annealing, the reaction mixture from the annealing step may be transformed into host cells. The host cells should be adapted to the acceptor nucleic acid such that replication of the acceptor nucleic acid is possible in the host cell. Thus, the acceptor nucleic acid should have an origin of replication that can be recognized by DNA polymerase present in the host cell. It is advantageous that the acceptor nucleic acid contains in its vector backbone a selectable marker allowing selection for host cells containing the acceptor nucleic acid. The host cell will fill gaps in the annealed acceptor nucleic acid and will cleave overhangs of the DNA or the acceptor nucleic acid not involved in annealing. Clones of host cells may be obtained, and repaired vector DNA may be isolated from clones of host cells, e.g. for sequencing the nucleic acid of interest inserted into the acceptor nucleic acid.

Figure 6:
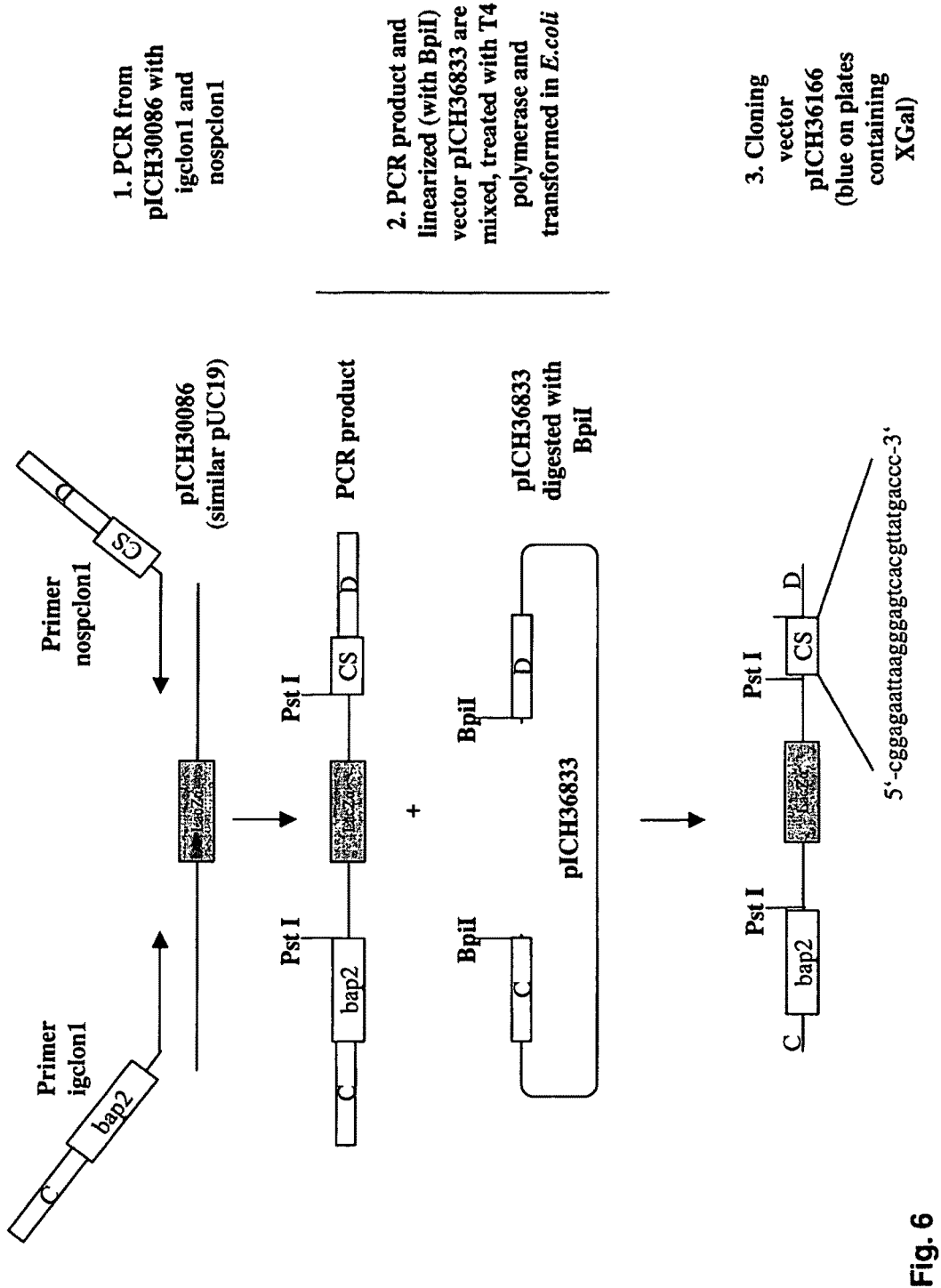
FIG. 6: Scheme showing the construction of clean cloning vector pICH36166. A PCR is performed using primers igclon1 and nospclon1 using pICH30086. Segments C and D of the primers are also present in the vector pICH36833. bap2 is an adaptor sequence to be inserted into the acceptor vector pICH36166 to be produced. CS stands for catching sequence that is an example for sequence segment K2. The nucleotide sequence of CS is shown and referred to herein as SEQ ID NO: 2. The PCR product can be inserted in vector pICH36833 by homology cloning involving treatment of both the PCR product and pICH36833 with the exonuclease activity of T4 polymerase.

The adaptor sequence as well as segment K2' determine the suitability of a given acceptor nucleic acid for inserting a given amplified DNA. Different acceptor nucleic acids may have to be made for amplified DNAs differing significantly in the nucleotide sequence at the first end or in segment K2. However, construction of the acceptor nucleic acid is straightforward. FIG. 6 shows a strategy therefor, wherein the adaptor sequence (bap2 in this example) and segment K2' (CS in this example) are provided to the acceptor nucleic acid via primers (igclon1 and nospclon2 in FIG. 6). Cloning by homology may be used for inserting the PCR product into a vector backbone (pICH36833 in FIG. 6). The acceptor nucleic acid (pICH36166 in FIG. 6) can be linearized with restriction endonuclease PstI. It is convenient to use the same adaptor sequence at the first end of the amplified DNA and the acceptor nucleic acid for cloning projects of sequences of interest having different segments K2.

In the following, the template used in the PCR step as well as ways of obtaining it are described. The template nucleic acid comprises the nucleic acid of interest and thus comprises, in this order, at least segment U, segment K2 and a segment homologous to segment K3. As above, the nucleotide sequence of segment K2 is essentially known. That of the segment homologous to K3 is also essentially known so that the reverse primer can be designed to hybridize to the segment homologous to segment K3 of the template. If the nucleotide sequence at the other end of the nucleic acid of interest in the template is known, the forward primer can be designed to hybridize for PCR purposes to first end of the template.

In an important embodiment, the sequence of interest to be inserted into an acceptor nucleic acid has at its first end sequence segment U the nucleotide sequence of which is not known. In this case, it is not possible to design a specific forward primer and to prepare an acceptor nucleic acid having at its first end a sequence segment homologous to the first end of the nucleic acid of interest. Various solutions to this problem have been described in the prior art that may be used for the present invention. Starting material for this embodiment can be genomic DNA isolated from eukaryotic or prokaryotic cells. In an alternative embodiment, the starting material may be RNA isolated from eukaryotic or prokaryotic cells. The starting material can also be, or contain in the total isolated RNA, mRNA from eukaryotic or prokaryotic cells.

Figure 4:
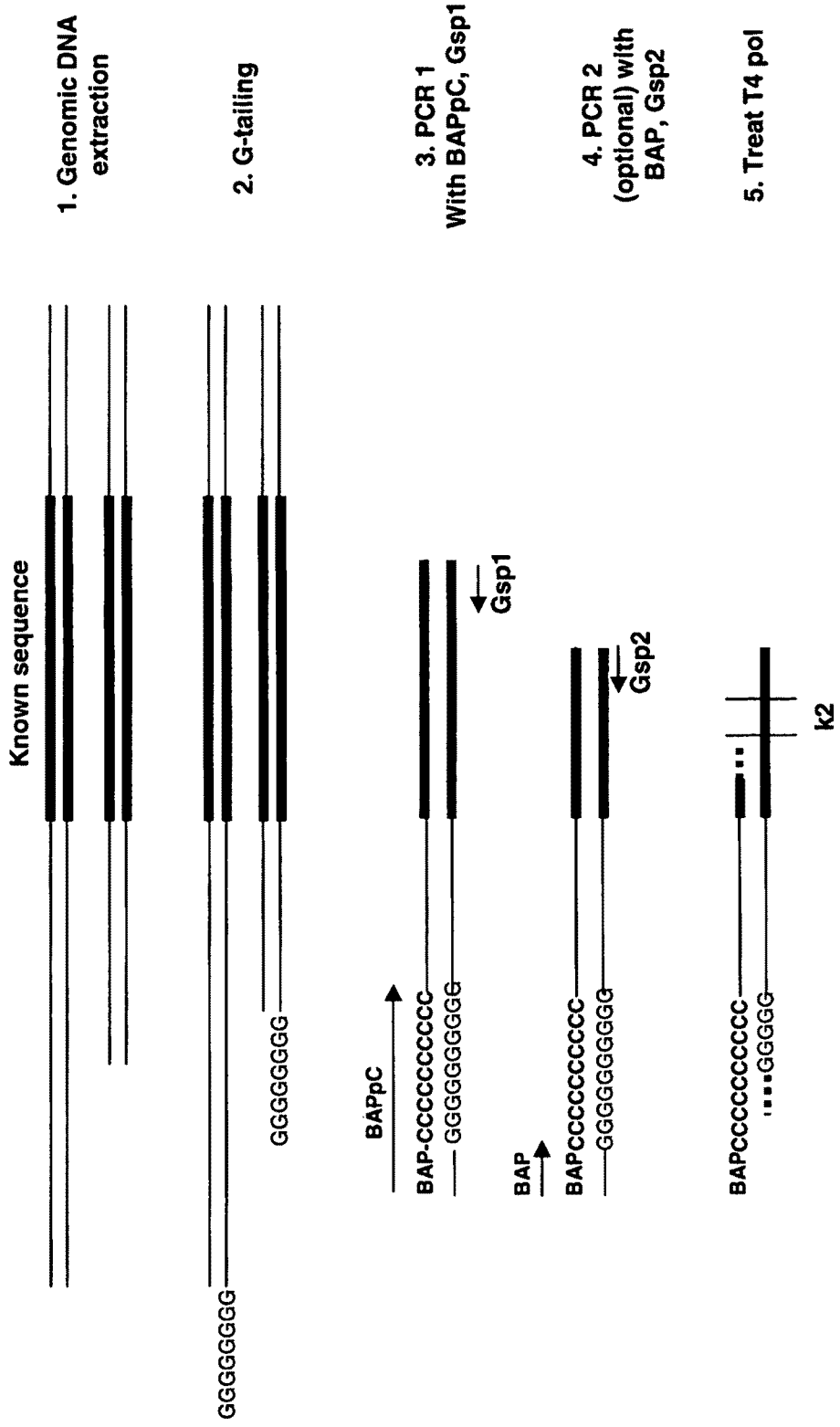
FIG. 4: Cloning of flanking sequences from a DNA template: preparation of insert for clean cloning, strategy 1. Genomic DNA is isolated that generally contains a plurality of different fragments of genomic DNA (two different double-stranded DNA fragments are shown at the top). In the next step, genomic DNA fragments are G-tailed using terminal transferase at sites where DNA is broken during the extraction procedure. One (or two nested) PCR is (are) performed. Then, the amplified PCR product is subjected to exonuclease treatment to obtain 5' single-stranded overhangs. Both PCR1 and PCR2 are generally performed in this strategy, since the ratio of desired PCR products to unspecific PCR products may not be satisfactory if only one PCR is performed.

In one embodiment wherein the nucleic acid sequence is DNA (e.g. in a preparation of genomic DNA), a primer binding sequence is attached to a nucleic acid sequence having at one end nucleic acid sequence segment U of unknown nucleotide sequence (see FIG. 4 for an illustration). The primer binding sequence may be a homooligomeric nucleotide sequence segment that is attached to segment U using terminal deoxyribonucleotide transferase and NTPs of the type of the desired homooligomeric tail to be attached. In a preferred embodiment, the homooligomeric nucleotide sequence segment (or "tail") consists of guanine bases, and the attachment using terminal deoxyribonucleotide transferase is known as "G-tailing". Instead of GTPs, other NTPs such as ATP, CTP or TTP may be used. Once a primer binding sequence is attached, the nucleotide sequence of the first end of the obtained nucleic acid of interest is known, and a suitable forward primer of complementary sequence may be designed for the PCR. The primer binding sequence should have a length of at least 10 nt. However, it is preferred that the sequence used for homology cloning at the first end of the DNA into the acceptor nucleic acid is longer than this length. Therefore, the forward primer used may comprise at its 5'-end an adaptor sequence segment in addition to a sequence segment complementary to the primer binding sequence. The amplified DNA will then contain the adaptor sequence at its first end that will be rendered single-stranded in the exonuclease treatment step. The acceptor nucleic acid will be provided with a sequence segment homologous to the adaptor sequence such that exonuclease treatment of the acceptor nucleic acid generates a single-stranded overhang at the first end of the acceptor nucleic acid that is complementary to the single-stranded overhang at the first end of the amplified DNA.

In the embodiment of the previous paragraph, it is advantageous to conduct a pre-amplification step by PCR (referred to as "PCR1", step 3 in FIG. 4). The PCR amplification step of the invention is then the second PCR (referred to as "PCR2 in FIG. 4). In this embodiment, the reverse primer used in the second PCR corresponds to segment K3 of the amplified DNA. The reverse primer used in the first PCR also binds to a sequence segment of known nucleotide sequence of the PCR template of the first PCR.

Figure 5:
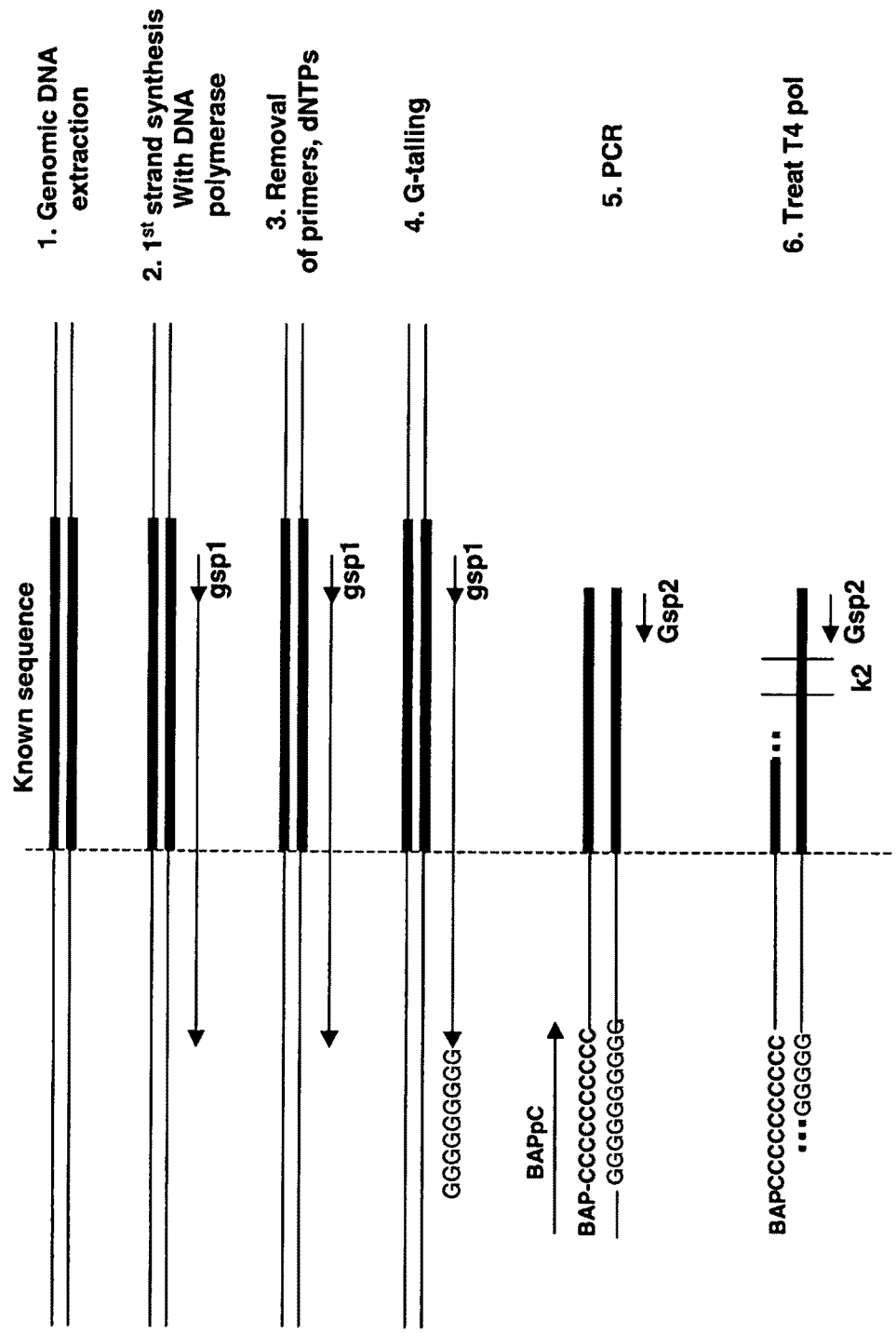
FIG. 5: Cloning of flanking sequences from a DNA template: preparation of insert for clean cloning, strategy 2. Rather than relying on broken DNA ends in genomic DNA as in strategy 1 (FIG. 4), linear amplification is made by PCR using only a gene-specific primer gsp. This product is then G-tailed using terminal transferase. Then, a PCR is performed using primers BAPpC and a second gene specific primer Gsp2, followed by exonuclese treatment.

In another embodiment wherein the nucleic acid sequence is DNA (e.g. in a preparation of genomic DNA), a first strand synthesis is performed on DNA such as genomic DNA using a primer binding to a known sequence (see FIG. 5 for an illustration). After removal of primers and dNTPs, a primer binding sequence may be attached to the 3'-end of the synthesized first strand. The following steps may be the same as in the previous embodiment illustrated in FIG. 4. However, no pre-amplification is generally required.

In an alternative embodiment wherein the nucleic acid sequence is DNA (e.g. in a preparation of genomic DNA), an adaptor sequence of sufficient length is attached by ligation to a nucleic acid sequence comprising, in the following order, the nucleic acid sequence segment U at the first end of the nucleic acid sequence, a nucleic acid sequence segment of known sequence K2 and a nucleic acid sequence segment of known sequence K3 before the PCR amplification step. It is not necessary to introduce an adaptor sequence into the first end via the forward primer. The forward primer used in the PCR is designed so as to bind to the adaptor sequence attached. Preferably, in this embodiment, the forward primer terminates at its 5'-end in the adaptor sequence attached to the nucleic acid.

In a further embodiment, TAIL-PCR as described by Liu et al in Biotechniques 43 (2007) 649-656 is employed in the PCR amplification step.

In an important embodiment, a cDNA of an RNA sequence of interest such as an mRNA sequence of interest is inserted into an acceptor nucleic acid, cf. FIG. 2. In this case, the starting material for the process of the invention is RNA. After having isolated RNA from eukaryotic or prokaryotic cells, a cDNA strand of the RNA is generated by reverse-transcription using a gene specific primer ("gsp1" in FIG. 2). If the RNA is mRNA, an oligo-dT primer may be used alternatively for reverse-transcribing the mRNA. The skilled person understands that many more products are obtained if an oligo-dT is used as a primer for the synthesis of cDNA strands compared to a case where a gene specific primer is used on a sample of cellular mRNAs. Use of an oligo dT primer instead of a gsp1 for first strand synthesis has the advantage that any unknown polymorphisms that may be present in segment K2 in mRNA from different individuals does not lead to failure of first strand synthesis of such polymorph. As a next step, the RNA template may then be digested and primer used for retro-transcription may be removed. The remaining steps of the process of the invention may be the same as described above. FIG. 2 illustrates in step 6 a first PCR and an optional second nested PCR. If two PCR reactions are performed on the DNA template, the second PCR is considered the amplification step of the invention and the reverse primer of the second PCR defines segment K3 of the PCR product. Generally, the last PCR amplification is considered the amplification step of the invention. If only one PCR is performed on the DNA template, this one PCR is considered to be the amplification step of the invention.

An alternative strategy to attach an adaptor to sequence segment U is to ligate an RNA primer to the 5' end of the mRNA using T4 RNA ligase as described in Trout, A. B., McHeyzer-Williams, M. G., Pulendran, B. and Nossal G. J. V., 1992, PNAS, Vol 89: 9823-9825. This modified RNA is then reverse-transcribed and used for PCR amplification as in other protocols described above.

An alternative strategy uses the template switching activity of Moloney murine leukemia virus reverse transcriptase to add an extra 2-4 cytosines to the 3' end of the newly syntesized cDNA strand upon reaching the cap-structure of the mRNA as described in U.S. Pat. No. 5,962,272. The resulting cDNA may be made to contain an adaptor sequence at the side of segment U is. This strategy does not require G-tailing with terminal transferase, and the product can be used directly for PCR as in other protocols.

If the starting material of the process of the invention is DNA such as genomic DNA isolated from eukaryotic or prokaryotic cells, various strategies may be used for providing the template for the PCR reaction of the invention. Two possible strategies are shown schematically in FIG. 4 and FIG. 5. In the strategy depicted in FIG. 4, fragments of genomic DNA are used directly for attaching an adaptor or a homooligomeric tail. It has surprisingly been found by the present inventors that it is not necessary to apply any measures for promoting DNA fragmentation such as DNase treatment or applying shear stress. Instead, genomic DNA as isolated under mild conditions by a commercial kit for genomic DNA isolation may be used. Fragments of genomic DNA will be substantially larger compared to a case where DNA fragmentation is induced. Since smaller fragments are preferentially amplified by PCR, having larger fragments of genomic DNA means that less background of unspecific PCR products is produced during PCR amplification than in the prior art methods. Still, it is possible to amplify essentially all nucleic acids of interest, since for most sequences of interest there will be fragment of genomic DNA in a typical preparation that is located close enough to an end of a fragment for allowing efficient PCR amplification.

For identification of unknown sequences in DNA, for example transgenes or transposon insertions, or for chromosome walking, various protocols have been described in the literature. These strategies fall into several classes.

In the first class, DNA is digested with an enzyme and an adapter ligated to the ends. Flanking sequences are then amplified using known sequence specific primers (gsp) and adapter primers. Two nested PCRs are usually performed using two nested known sequence specific primers. A major drawback of protocols that rely on digestion of DNA with enzymes is that it is not known whether an enzyme cuts in the proximity of the known sequence, and it is therefore necessary to use several enzymes in parallel to be sure that one will provide results (produce a fragment that is not too short and have sufficient information, or not too long since it would not be amplified by PCR). The PCR product can then be directly sequenced. However, this will not produce information if more than one insertion is present and both flanking sequences have been amplified. This mixture of PCR products can be cloned and several plasmids sequenced in order to get the two flanking sequences.

However, one possible problem when analyzing flanking sequences using an adaptor ligated to DNA ends produced by restriction digest is that one cannot be sure that all flanking sequences of all insertions in this genome have been determined. This is because PCR products obtained for various flanking sequences will all have different sizes, and competition during PCR will mean that the smallest will be amplified preferentially. One solution will be to perform sequence identification with several different enzymes in parallel, which will increase the amount of work required for each line to be analyzed.

One solution to this problem is to not digest DNA using restriction enzymes but use random fragmentation (partial digestion of DNA using a frequent cutter, use of DNaseI, or sonication). These strategies will be less prone for non-random amplification.

A second class of protocols is based on inverse PCR (IPCR) (Ochman H., Gerber A. S., & Hartl D. L., 1988, *Genetics*, 120:621-623). DNA is digested with a restriction enzyme and then religated using DNA ligase. At low DNA concentration, the most frequent ligation event is circularization of DNA fragments. This allows amplification using two gene-specific primers. An advantage of iPCR is that flanking sequences can be identified after a single PCR (depending on the size of the host genome) or two nested PCR. The drawbacks are as described for the previous methods: use of several different enzymes will be required to find all insertions.

A third class of methods is based on PCR amplification using a known region-specific primer (gsp) and a non-specific random primer. One example of such approach is TAIL PCR. TAIL PCR requires three rounds of nested PCR and several parallel reactions to with different sets of random primers (Yao-Guang Liu & Robert F. Whittier, 1995, *Genomics*, 25:674-681). One advantage of this protocol is that it is a PCR-only method and can therefore be automatized. A drawback is that it will not always work and will not identify all flanking sequences when multiple insertions are present.

Moreover, it is a quite tedious protocol since each sample requires many PCR amplifications.

We have developed a protocol that allows identification of all the insertions present in a genome in a single experiment. Genomic DNA is prepared using a standard kit with a column. The DNA produced using standard commercial kits is generally composed of fragments ranging on average from 10 kb to 25 kb. This means that for any known sequence, a DNA break point will occur within from 0 nt to 25 kb to any given sequence, on average. We therefore take advantage of this observation and directly tail genomic DNA broken ends with a G tail using terminal transferase (FIG. 4), which is extremely simple to perform and is extremely useful, as shown by our results. As is done for amplification of cDNA ends, a first PCR is performed using a BAPpC primer and a known sequence specific primer (gsp1). This first PCR will amplify the specific products, but also small non-specific fragments with BAPpC primer alone. This is because all genomic DNA fragments are tailed from both sides by terminal transferase. A second PCR is performed with a BAP primer and a nested known sequence-specific primer (gsp2) in order to enrich the ratio of gene specific-sequence to non-specific sequences. Even after this second PCR, it is expected that both specific and non-specific products will be amplified. Therefore, in order to clone only the specific products, we use the clean-cloning process of the present invention. A linear cloning vector is prepared containing at one end homology to the adaptor and at the other end homology to the sequence located just upstream of the gsp2. This vector and the insert are treated by T4 polymerase. Only gene-specific products are obtained.

This protocol is extremely reliable: in only one cloning experiment all flanking sequences from all insertions can be identified. The totally random tailing allows quantitative amplification of flanking sequences; for example a genome containing one insertion homozygous and the other heterozygous will identify the first insertion in two third of the sequenced plasmids and the second insertion and the remaining one third of sequences. Moreover, clean cloning allows to directly sequence all plasmids obtained without prescreening for recombinant plasmids containing a specific insertion.

An alternative protocol for cloning of flanking sequences consists of performing as a first step, a few amplification cycles with only one primer, the gene-specific primer (gsp1, FIG. 5). The PCR product is then tailed using terminal transferase and then one or two PCR are performed. The PCR fragment is then cleaned-cloned as previously described.

In example 4 we reliably identified sequences flanking T-DNA insertions in transgenic plants. In case of RNA sequences identification (example 2), we successfully identified the sequences of variable regions of tumor-specific immunoglobulins that are displayed on the surface of malignant B-cells. The immunoglobulins, especially their variable regions can be used as individualized vaccine antigens for treatment of Non-Hodgkin Lymphoma (Inoges et al., 2006, *J Natl Cancer Inst.*, 98:1292-1301; McCormick et al., 2008, *Proc. Natl. Acad. Sci. USA*, 105:10131-10136).

EXAMPLES

Example 1

Construction of Clean Cloning Vectors a) construction of pICH36166

The lacZ alpha fragment was amplified by PCR from plasmid pICH30086 (identical to pUC19 except that the bla gene providing ampicillin resistance was replaced by a Kanamycin resistance gene). Primers for amplification were Igclon1 (SEQ ID NO: 6) (5'-GGA GGG TTG AAG ACT TGT CCA GAG CCG TCC AGC AAC TGC AG GCAGCTGGCACGACAGGTTTC-3') and nospclon1 (SEQ ID NO: 7) (5'-GAT CCT AGA TGT GGA AGA CTT TAC CGG GTC ATG ACG TGA CTC CCT TAA TTC TCC GCT GCA G CGCGCGTTTCGGTGATGACG-3') (FIG. 6). The 3'-part of both primers (underlined) is specific for the lacZ alpha fragment in pICH30086. This sequence is preceded by a PstI recognition site (italics). The middle part (dotted line bold) contains the homologous sequences for clean cloning (bap2 in Igclon1 and the 'catching sequence CS', in this case Nos promoter-specific in nospclon1). The 5'-part of each primer is homologous to the ends of a linearized vector used for cloning, in this case pICH36833 (sequence regions C and D in FIG. 6). It should be mentioned that the clean cloning vector can in fact be prepared from any standard cloning vector other than pICH36833, the only requirement is to select sequences C and D for the primer design that match the chosen vector in the region flanking the site used to linearize it.

The LacZ fragment amplified from pICH30086 was amplified by PCR in a 50 µl volume. The PCR product was purified through a column (NucleoSpin Extract II, Macherey-Nagel, Düren, Germany; elution volume 50 µl). pICH36833 was cut with BpiI and column-purified, too. To perform the T4 cloning, 2 µl of the PCR product, 1 µl of BpiI-digested vector, 2 µl 10× T4 polymerase buffer (New England Biolabs, Ipswich Mass., USA), 0.5 µl T4 DNA polymerase (NEB, 20 units/µl) and 14.5 µl water were mixed and incubated for 5 minutes at room temperature. The mix was transformed in chemically competent *E. coli* DH10b by heat shock transformation, and plated on media containing X-Gal and carbenicillin (pICH36833 has a bla gene providing carbenicillin resistance). Positive clones can be detected using blue/white selection, with blue colonies containing the desired vector construct (pICH36833 does not have a functional LacZ gene, but the resulting clean cloning vector does). The region containing Bap2 and the 'catching sequence' is sequenced before use to check that the cloning sequence Bap2 and the 'catching sequence' are correct.

As mentioned above, the resulting clean cloning vectors contain a lacZα cassette for blue-white selection flanked by two PstI sites, and then flanked on the 5' part of LacZ by a sequence corresponding to the G-tail specific primer Bap2 (SEQ ID NO: 8): gtccagagccgtccagcaac and on the 3'-side by a 20-52 bp catching sequence. In case of pICH36166, the catching sequence corresponds to part of the Nos terminator. For clean cloning, clean cloning vectors are first digested with PstI, which cleaves on both sides of the LacZ fragment, producing a linear vector containing at both ends sequences of the Bap2 and of the catching sequence. This linear fragment is then ready for exonuclease treatment and cloning (see below).

b) Construction of Other Clean Cloning Vectors

All other clean cloning vectors can be prepared with exactly the same protocol as described above, with the only exception that the primer nospclon1 has to be replaced by a different primer in which the sequence of the catching sequence is changed to whatever sequence the user desires to 'catch'.

Example 2

Identification of the Variable Region of an Immunoglobulin a) General Description of the Methods RNA was isolated from 0.2 ml tumor cell suspensions (5-15 million cells) of lymph node biopsies from Non- Hodgkin lymphoma patients using the RNeasy kit (Qiagen) according to manufacturer's protocol. The RNA was eluted using 40 µl RNAse-free water. The quality of the RNA was tested by agarose gel electrophoresis and the concentration was measured with a NanoDrop ND-1000 (Thermo Scientific). 0.5-1.0 µg RNA were reverse transcribed into cDNA using the SuperScript III reverse transcriptase kit from inVitrogen, and using an Oligo dT20 (Invitrogen). A 10 µl mix containing the RNA, 1 mM dNTP, 5 µM Oligo dT20 in RNAse-free water were denatured for 5 minutes at 65° C. in a PCR thermo cycler (BIO-RAD). The mix was chilled down for at least 1 minute at 4° C., then 2 µl 10× RT buffer, 4 µl 25 mM $MgCl_2$, 2 µl 0.1 M DTT, 1 µl RNase OUT and 1 µl SuperScript III reverse transcriptase were added. The reaction mix was incubated in a PCR thermocycler for 50 minutes at 50° C. and then heat inactivated at 85° C. for five minutes. The resulting cDNA was not treated with RNaseH, but column-purified (MN Extract II kit, Machery-Nagel) and eluted with 25 µl elution buffer. 10 µl of column-purified cDNA was used for G-tailing using 5 units terminal transferase (NEB), 0.25 mM dGTP, 0.25 mM $CoCl_2$ in 1× NEB buffer 4 in a 50 µl reaction mix. The G-tailing reaction was incubated for 45 minutes at 37° C. in a PCR thermo cycler. Terminal transferase was inactivated for 15 minutes at 70° C. The inactivated G-tail reaction mixture was directly used for a PCR to amplify immunoglobulin fragments. The PCR for amplification of antibody fragments from G-tailed 1st strand cDNA was carried out using a G-tail-specific primer (Bap2pc (SEQ ID NO: 9: gtccagagccgtccagcaa cccccccccccccc) and immunoglobulin specific primers (see below the description for specific amplifications) derived from the constant region. The reaction was set up out using Hot Start Taq DNA polymerase (Fermentas) in a 50 µl reaction mix containing 1 µl G-tailed cDNA, 0.2 mM dNTP, 2 mM $MgCl_2$, 2 units Hot Start Taq, 0.2 µM G-tail specific primer, 0.2 µM immunoglobulin constant region-specific primer. The PCR amplification used a 4 minutes step of activation of the Hot Start Taq and denaturing at 95° C. and 36 cycles of 20 seconds denaturing at 95° C., 30 seconds annealing at 58° C. and one minute elongation at 72° C. 10 µl of the PCR reaction were analyzed by agarose gel electrophoresis. The PCR product is then column purified (using the Machery-Nagel MN Extract II kit) to remove primers and the remaining dNTPs that could inhibit the 3'-5'exonuclease activity of T4 DNA polymerase during the next step. The PCR product is eluted from the column in 50 µl of elution buffer.

Clean cloning vectors were isolated from 1 ml stationary phase *E. coli* DH10B using the Nucleospin Plasmid Quick-Pure kit (Macherey-Nagel) according to the manufacturer's protocol. Vector DNA was eluted with 50 µl elution buffer. 3 µl of the purified vector DNA was digested in a 30 µl reaction with PstI, heat inactivated for 20 minutes at 80° C. and analyzed by agarose gel electrophoresis. For T4 clean cloning, T4 DNA polymerase (NEB) is used to chew the ends of the vector and of the PCR product, resulting in single-stranded regions of DNA at the ends of insert and vector fragments. To perform the T4 clean cloning, 2 µl of the PCR product, 1 µl of the PstI-digested T4 clean cloning vector, 2 µl 10× T4 polymerase buffer (NEB), 0.5 µl T4 DNA polymerase (NEB, 20 units/µl) and 14.5 µl water were mixed and incubated for 5-15 min at room temperature. Reactions were chilled on ice for 1 minute and directly transformed into 100 µl of chemo-competent *E. coli* DH10B cells. Clones were selected on LB agar plates supplemented with carbenicillin and X-Gal. Blue-white selection was used to identify clones containing inserts (white), while blue clones carry undigested T4 clean cloning vectors. To analyze efficiency of cloning of immunoglobulin sequences, 48 randomly chosen clones of every cloning were sequenced using a vector primer.

b) Cloning of Immunoglobulin Sequences: Results

Figure 7:
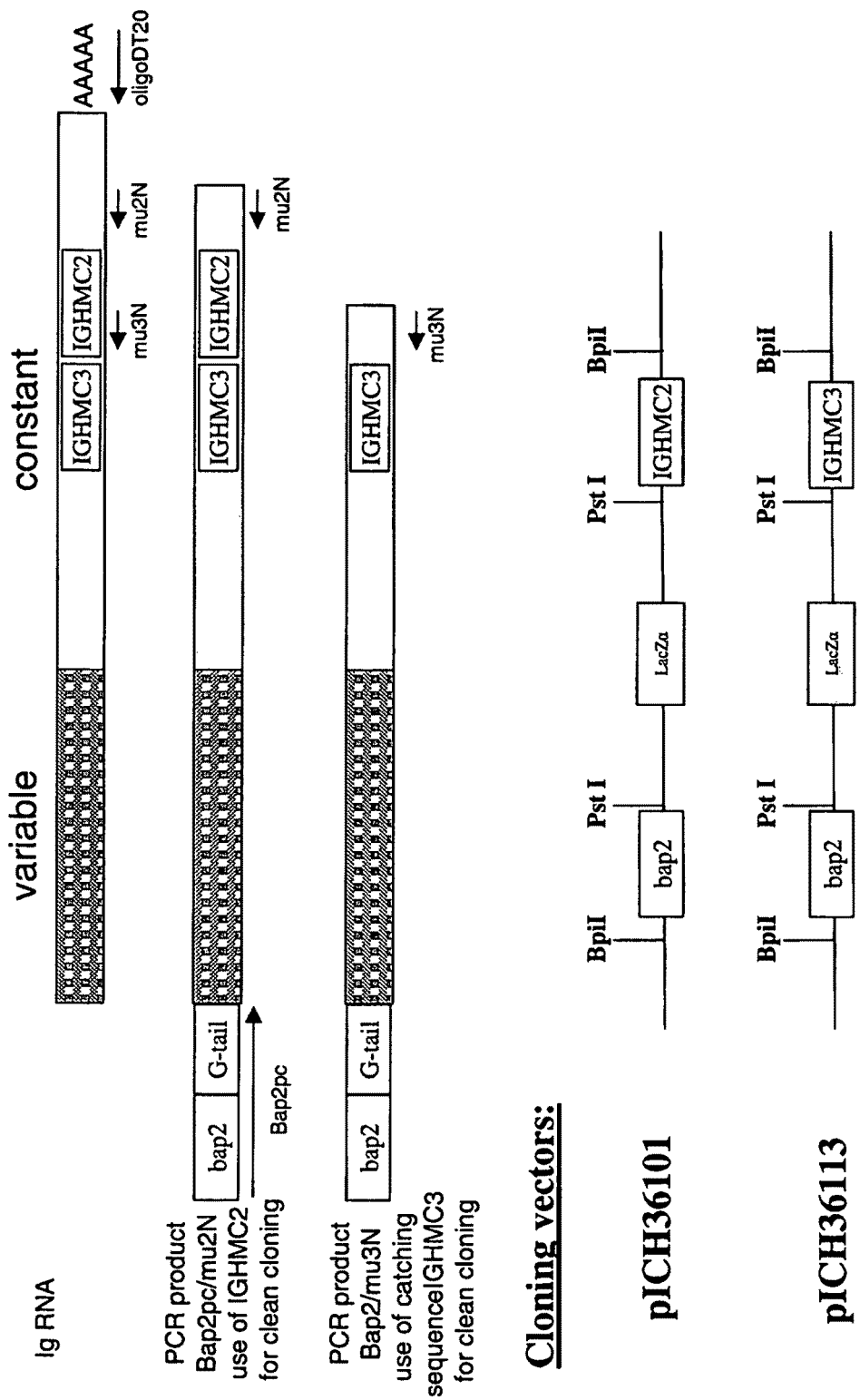
FIG. 7: Structure of the IGM antibody RNA with constant and variable sequences, G-tailed PCR products, and clean cloning vectors used in the examples.

Two tumor samples were analyzed, both containing a tumor-associated immunoglobulin of the isotype IgM,K (heavy chain Mu, light chain Kappa). For each biopsy and for both the light chain and the heavy chain, two independent PCR products were performed with different primers and cloned. This was done to make sure that the correct tumor-associated sequence was determined. Since two different constant region-specific primers were used (separately) for each sequence identification, two corresponding separate clean cloning vectors were also made. For example, two clean cloning vectors were made for the heavy chain: pICH36101 and pICH36113 (FIGS. 7 and 8) and two clean cloning vectors made for the light chain, pICH36078 and pICH36083 (FIG. 9). In each case, the catching sequence does not overlap with the primer used for amplification. Note that the catching sequence does not have to be exactly upstream of the primer used for amplification; in fact primer used for amplification and catching sequence can be separated by 10, 20 or even 30 nucleotides, and clean cloning will still work.

For sample 1 (T096) PCR products obtained by amplification with primer Mu2N (SEQ ID NO: 10) (tc tgc tga tgt cag agt tg) were cloned into the IgM vector pICH36101, and products obtained from amplification with primer Mu3N (SEQ ID NO: 11) (aag tcc tgt gcg agg cag) cloned into IgM vector pICH36113. 48 and 47 resulting *E. coli* clones, respectively, were analyzed by sequencing. 92 sequences could be derived, three sequence reactions failed. 87 of these sequences were found to correspond to full length fragments containing 5'UTR, leader, variable region and partial constant region of the cloned immunoglobulins. The five other sequences also corresponded to immunoglobulins but were not full length. The cloning efficiency for immunoglobulin sequences was 100% and 95.6% of the sequences corresponded to full length fragments.

For sample 2 (T104) PCR products obtained by amplification with primer Mu2N were cloned into the IgM vector pICH36101, and products obtained from amplification with primer Mu3N cloned into IgM vector pICH36113. 48 resulting *E. coli* clones each were analyzed by sequencing. 96 sequences could be derived. 89 of these sequences correspond to full length fragments containing 5'UTR, leader, variable region and partial constant region of the cloned immunoglobulins. The seven other sequences also corresponded to immunoglobulins but were not full length. The cloning efficiency for immunoglobulin sequences was 100% and 93.7% of the sequences corresponded to full length fragments.

For sample 1 (T096) PCR products obtained by amplification with primer KC2N (SEQ ID NO: 12) (GGA GGG CGT TAT CCA CCT TCC) were cloned into the IgK vector pICH36078, and products obtained from amplification with primer (KC3N (SEQ ID NO: 13) (tca gca ggc aca caa cag agg) cloned in vector (pICH36083). 48 resulting *E. coli* clones each were analyzed by sequencing. 95 sequences could be derived one sequence reaction failed. 91 of these sequences correspond to full length fragments containing 5'UTR, leader, variable region and partial constant region of the cloned immunoglobulins. The four other sequences also corresponded to immunoglobulins but were not full length. The cloning efficiency for immunoglobulin sequences was 100% and 95.8% of the sequences corresponded to full length fragments.

For sample 2 (T104) PCR products obtained by amplification with primer (KC2N) were cloned into the IgK vector (pICH36078) and products obtained from amplification with primer (KC3N) cloned into IgK vector pICH36083. 48 resulting *E. coli* clones each were analyzed by sequencing. 96 sequences could be derived. 86 of these sequences correspond to full length fragments containing 5'UTR, leader, variable region and partial constant region of the cloned immunoglobulins. The 10 other sequences also corresponded to immunoglobulins but were not full length. The cloning efficiency for immunoglobulin sequences was 100% and 89.6% of the sequences corresponded to full length fragments.

Conclusion of these experiments: using T4 clean cloning, different types of immunoglobulin sequences belonging to different immunoglobulin classes could be cloned. The data could be used to successfully derive the exact tumor idiotype for the Non-Hodgkin follicular lymphoma samples.

Example 3

Determining Suitable Conditions for Exonuclease Treatment a) In Vitro Assay for Quantification of T4 Exonuclease Activity An assay was developed to determine the conditions suitable or optimal for T4 treatment. This assay consists of digesting linear DNA with T4 polymerase for a given time, then incubating 5 minutes at 80° C. to inactivate the T4 polymerase, then incubating 20 minutes at 25° C. with Mung Bean nuclease to digest single-stranded DNA ends generated by T4 polymerase. Digested DNA is then run on an agarose gel to compare the sizes of the resulting fragment with untreated linearized DNA. The DNA that we used is a digest of plasmid pICH10990, which results in four fragments of size 3595, 1563, 1158 and 125 bp (only the 3 larger fragments are useful since they are more visible on a standard ethidium bromide-stained agarose gel).

DNA was digested 10 minutes in the presence of T4 polymerase at 25, 20, 15 and 10° C. All incubations result in a shift in size (to smaller products), with the strongest shift with higher temperatures (FIG. 10). 10 minutes incubation at 25° C. results in digestion of approximately 100 to 300 nt (a smear is visible). Considering that digestion must take place at both ends of each fragment, digestion at each end is approximately 50 to 150 nt, indicating single-stranded regions of 50 to 150 nt at each end of the linear fragments after T4 treatment.

A second experiment was performed to find out whether addition of low concentrations of dNTPs can lower the rate of digestion of T4, to make digestion more user-friendly. Concentrations lower than 1 μM still allow single-stranded regions to be formed, while concentration of 10 μM and above completely inhibit formation of single-stranded regions.

b) Test of Different Digestion Times for T4 Clean Cloning of Immunoglobulin Variable Regions Antibody variable regions amplified from biopsy T078 were cloned using T4 clean cloning, according to the protocol described in previous examples. The insert was prepared with T4 digestion at room temperature from 5 to 20 minutes. White colonies were obtained with all 4 time points, but the maximal number of colonies was obtained with the 10 minute digestion (FIG. 11). Plasmid inserts from 170 colonies were sequenced (a random selection from the different time points), and all were found to contain immunoglobulin sequences.

Example 4

Isolation of Sequences Flanking T-DNA Insertions

Figure 12:
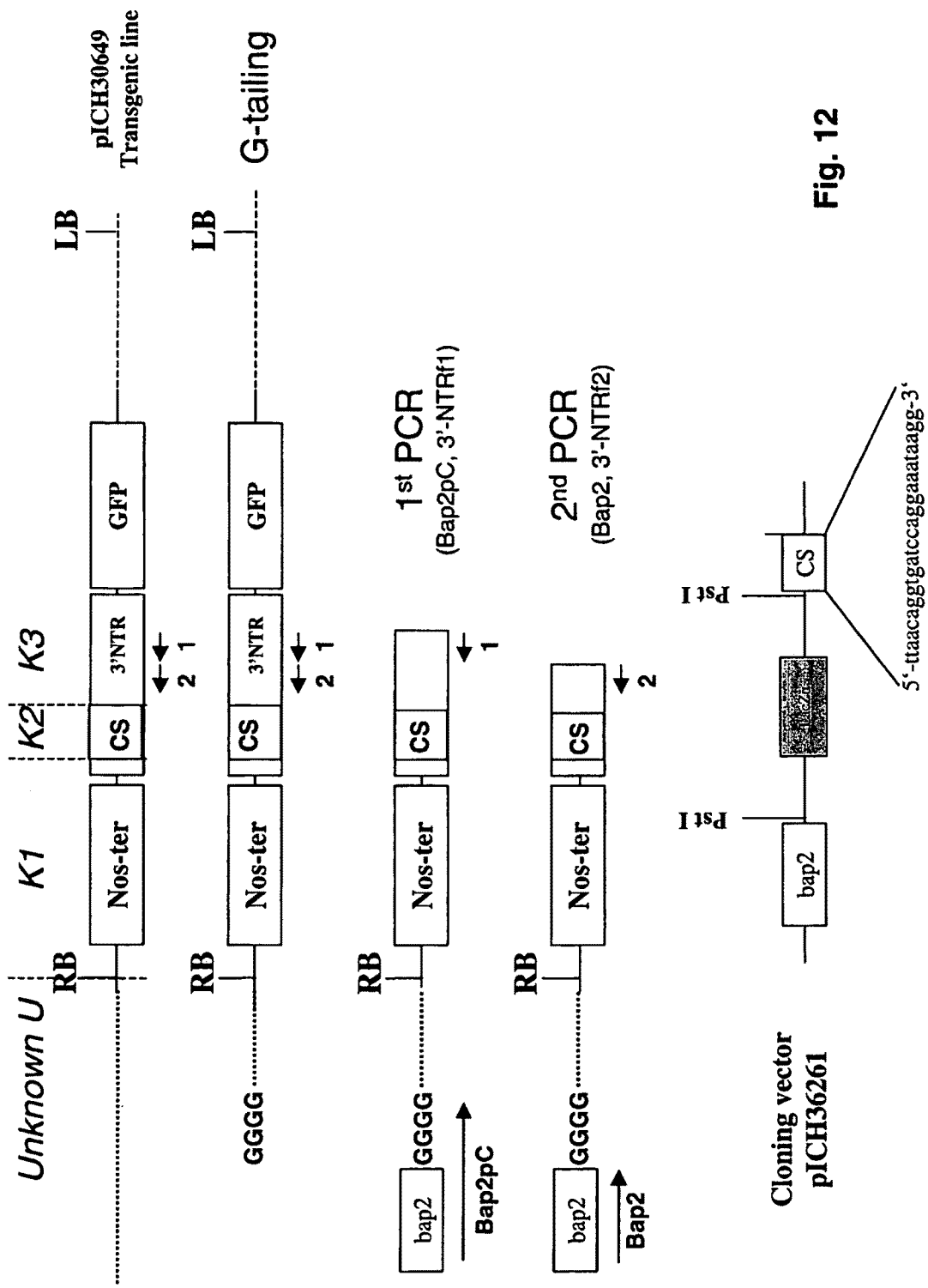
FIG. 12: Cloning of flanking sequence in DNA of a *Nicotiana benthamiana* plant transgenic for construct pICH30649. The T-DNA contains at the right border the Nos terminator and a viral-vector sequence (3' NTR). A 'catching sequence' (CS, equivalent to region K2) is defined in the 3'NTR and is cloned in a cloning vector pICH36166. bap2: adaptor sequence. "unknown" indicates a sequence segment of unknown nucleotide sequence U. The catching sequence CS is referred to herein as SEQ ID NO: 5. 3'NTR: 3' non-translated region. Regions K1, K2 and K3 are indicated. K1 is a sequence segment of known nucleotide sequence between the unknown sequence segment U and sequence segment K2.

*Nicotiana benthamiana* plants nbi157-3, nbi158-3, nbi159-3 and nbi160-7 are transgenic plants made by *Agrobacterium*-mediated transformation of a construct (pICH30649) that contains at the right border Nos terminator sequences and 3' NTR untranslated sequences of a cr-TMV based viral vector (FIG. 12). Genomic DNA was isolated from 100 mg leaf material using the NucleoSpin® Plant II Kit (Macherey-Nagel) according the manufacturer protocol. As all DNA extraction protocols, this isolation procedure results in some shearing of the genomic DNA.

In the first test, G-tailing was done on genomic DNA using different amounts of DNA (0.1, 0.3 or 1 μg). DNA was G-tailed using 5 units terminal transferase (NEB), 0.25 mM dGTP, 0.25 mM $CoCl_2$ and 1× NEBuffer 4 in a 50 μl reaction mix. The G-tailing reaction was incubated for 45 minutes at 37° C. in a PCR thermo cycler. Terminal transferase was inactivated for 15 minutes at 70° C. 3'-NTR specific primers were used for 2 rounds of nested PCR. The first PCR was performed with bap2pC (SEQ ID NO: 9) (gtccagagccgtccagcaac ccc ccc ccc ccc c) and 3'-NTRf1 (SEQ ID NO: 14) (gcgcacgatagcgcatagtg), with the following PCR conditions: 4 minutes 94° C. followed by 35 cycles of 10 sec 94° C., 30 sec 58° C. and 90 sec 72° C., followed by 4 min at 72° C. The second PCR was performed with primers bap2 (SEQ ID NO: 8) (gtccagagccgtccagcaac) and 3'-NTRf2 (SEQ ID NO: 15) (atccgtaggggtggcgtaaac) with the same PCR conditions. As expected, a smear of PCR products is visible in both PCRs (FIG. 13). Products from both PCRs (starting from 0.1 μg of DNA) were column-purified (NucleoSpin Extract II kit, Macherey-Nagel, 25 ul of PCR product was purified and eluted in 25 ul of elution buffer) before cloning into clean-cloning vector (pICH36261).

Figure 14:
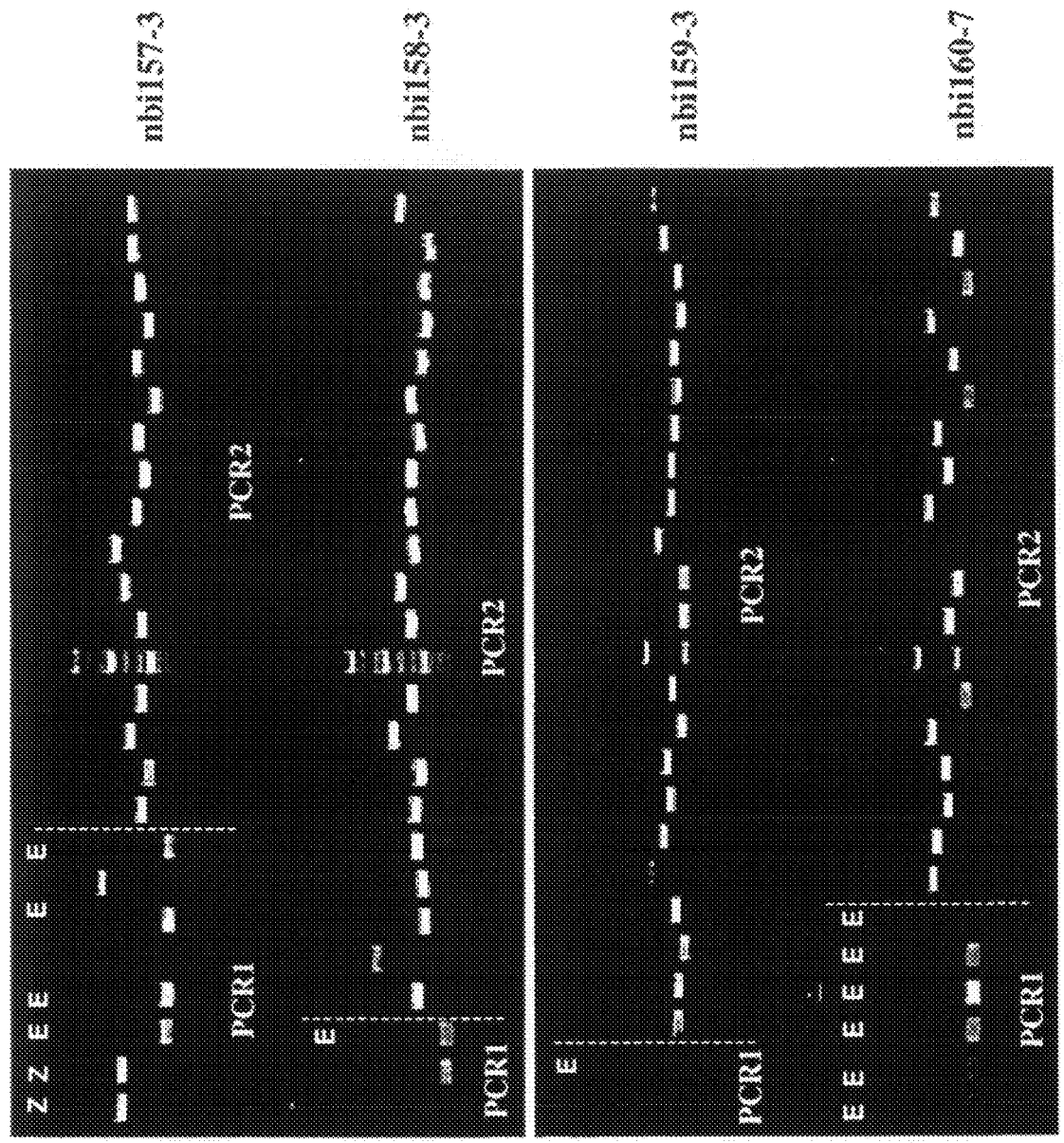
FIG. 14: Colony-PCR on cloned F-PCR products (pICH30649 transgene).

The cloning vector pICH36261 (FIG. 12) was cut with PstI and column-purified, too. The cloning reaction was set up with 1.5 μl vector (ca. 40 ng), 4 μl PCR-product, 2 μl 10× T4 polymerase buffer and 0.5 μl T4 DNA polymerase in a total volume of 20 μl. The reaction was incubated 5 min at room temperature and the entire mix transformed into 100 μl of chemically competent *E. coli* DH10b cells using heat shock transformation. Transformed cells were selected on medium supplemented with X-gal. White colonies were screened by colony-PCR (using two primers in the cloning vector flanking the insertion, kanseqf (SEQ ID NO:16): tggaaaaacgccagcaacgc, and kanseqr (SEQ ID NO: 17): tgtctcatgagcggatacat) for presence and size of the insert (FIG. 14). Empty vector (religated at the PstI site) gives a fragment of 295 nt. All larger PCR fragments indicate that the vector contains an insert.

There were only a few white colonies (0-6) after cloning of PCR1 products (indicating that only a low amount of specific products are present in the first PCR), whereas PCR2 products gave 20-120 white colonies. 24 colonies for each plant were screened by Colony-PCR (FIG. 14). Empty vector (or no product) is mostly found in clones of PCR1 (16 of 17 clones), whereas in PCR2 clones, inserts of ca. 150 bp up to >1000 bp are found.

78 clones were sequenced. One clone (from cloning after the 1st PCR) contained a non-specific product. All other 77 sequences were transgene-specific.

Example 5

Isolation of Sequences Flanking T-DNA Insertions with or without Pre-Amplification There are many ways by which flanking sequences of known DNA sequences can be amplified. We have exemplified one way in the previous example. However, clean cloning is suitable for PCR products that are obtained with any other strategy designed to amplify flanking sequences. Here we give an example to illustrate a slightly different amplification protocol. Clean cloning is however performed exactly as for the previous example.

Figure 15:
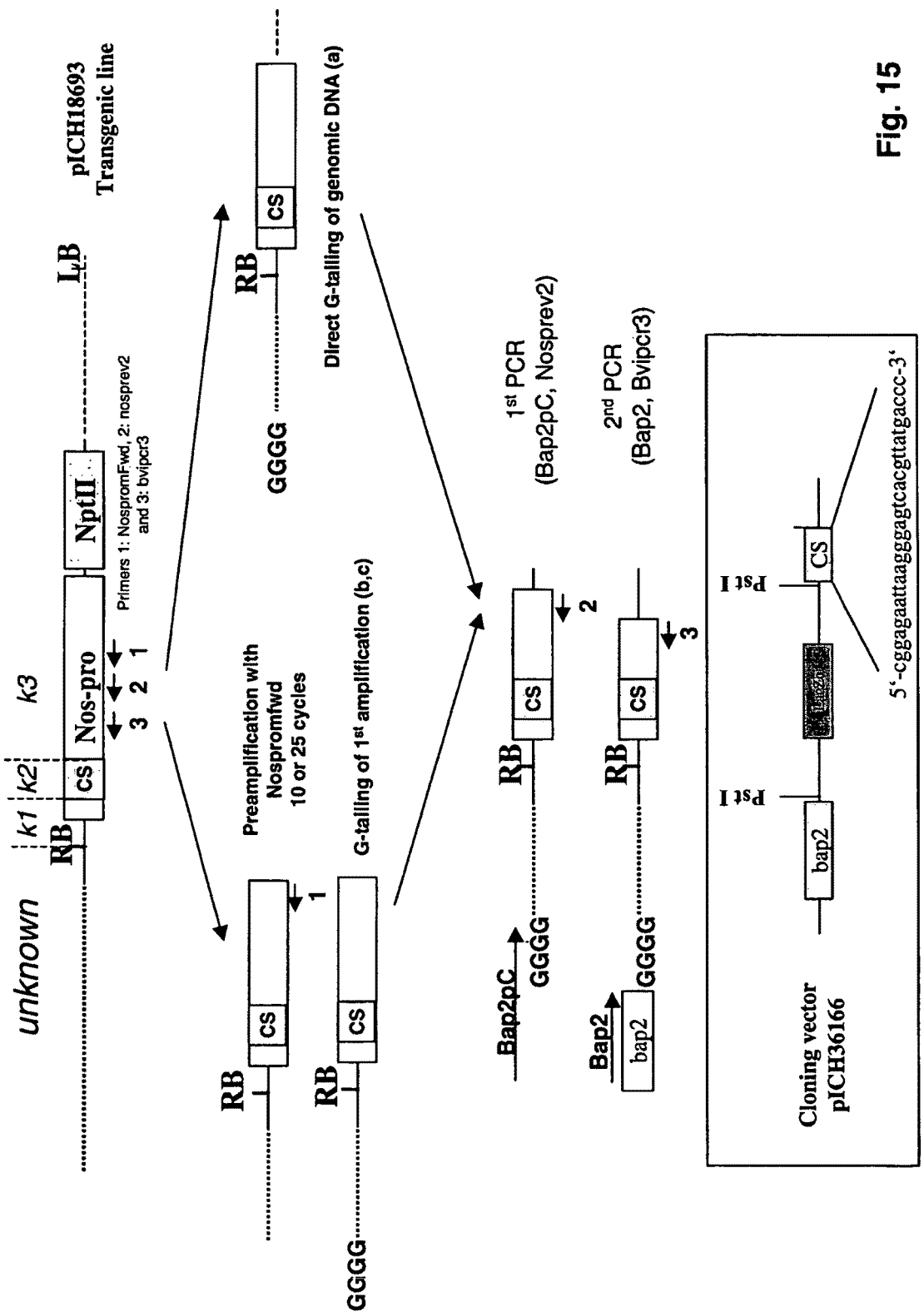
FIG. 15: F-PCR with and without pre-amplification. The catching sequence CS is referred to herein as SEQ ID NO: 2.

*Nicotiana benthamiana* plant nbi160-7 is transgenic for construct pICH30649, but also contains a second transgene from construct pICH18693 (FIG. 15). For this insertion, the Nos promoter is located near the right border. A cloning experiment was performed to compare clean cloning after direct G-tailing of genomic DNA or after G-tailing of the product of a linear preamplification done with a single primer.

Pre-amplification was done in a 50 µl reaction containing 100 ng of gDNA, dNTPs (0.2 mM each) and 0.2 µM of insert specific primer nospromfwd (SEQ ID NO: 18) (5'-TTT GCT AGC TGA TAG TGA CCT TAG GCG AC-3'). After the initial denaturation (2 min, 94° C.), 10 or 25 cycles of the following program were performed: 10 sec 94° C., 30 sec 58° C., 90 sec 72° C. Samples were purified through a column (NucleoSpin Extract II kit, Machery-Nagel, 50 µl of preamplification product was purified and eluted in 30 µl of elution buffer). The complete sample was used for attaching a G-tail to the free ends of the DNA using terminal transferase (NEB) in a 50 µl reaction volume as described in the previous example. G-tailing was also performed on 100 ng of genomic DNA without pre-amplification.

Figure 16:
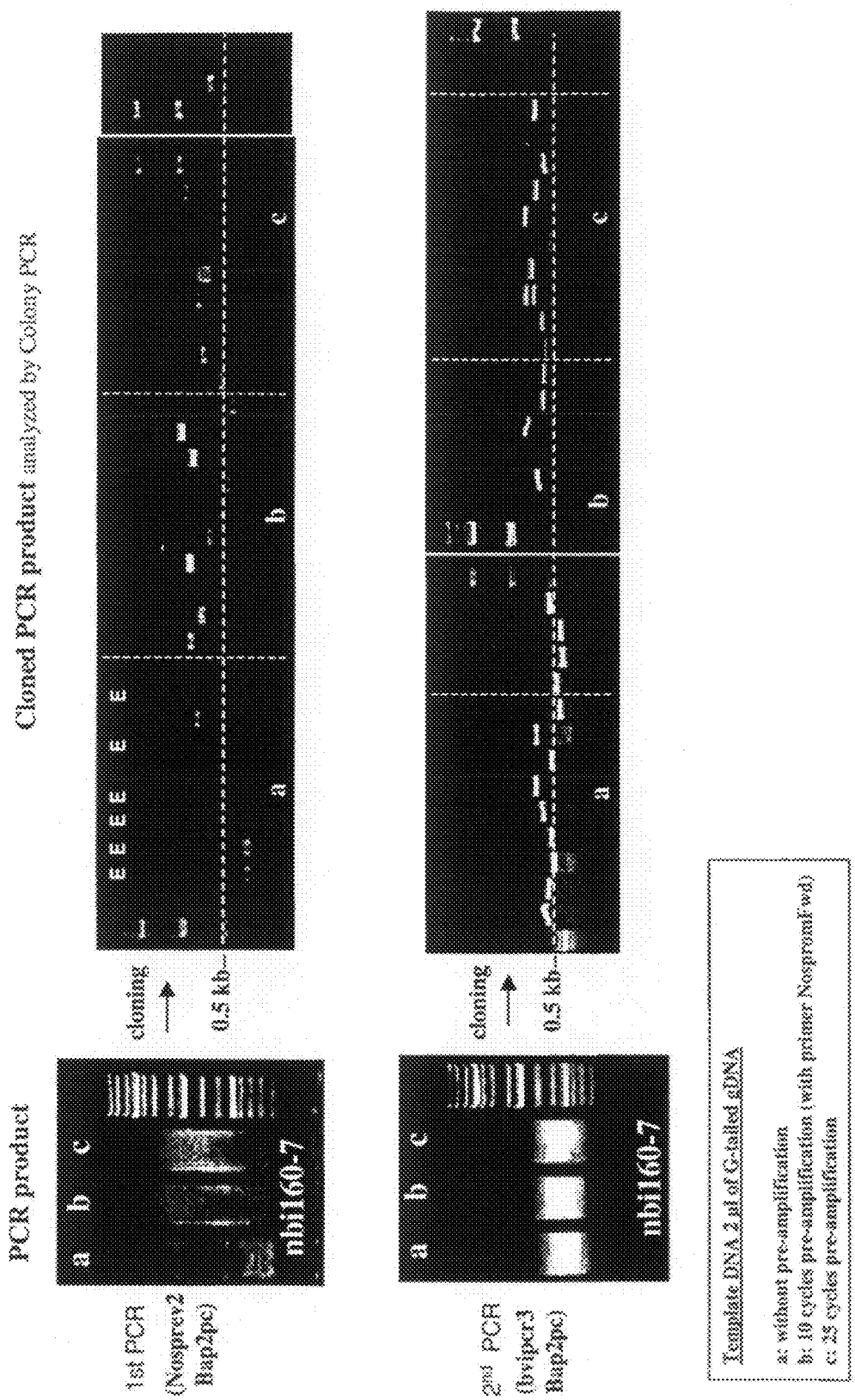
FIG. 16: F-PCR and cloning of flanking sequences of pICH18693 from transgenic plant nbi160-7.

Two µl of G-tailed DNA were then used in a 50 µl PCR reaction using pICH18693-specific primer nosprev2 (SEQ ID NO: 19) (5'-TGC GGT TCT GTC AGT TCC AAA CG-3') and the G-tail specific primer bap2pc (SEQ ID NO: 9) (5'-GTC CAG AGC CGT CCA GCA ACC CCC CCC CCC-3'). A nested PCR was performed with 1 µl of the nosprev2 PCR product in a 50 µl reaction using the nested specific primer bviper3 (SEQ ID NO: 20) (5'-CGG CTT GTC CCG CGT CAT C-3') and primer bap2 (SEQ ID NO: 8) (5'-GTC CAG AGC CGT CCA GCA AC-3'). The results of these PCRs are shown in FIG. 16.

Products from all PCRs were purified using the NucleoSpin Extract II Kit (Macherey-Nagel). The cloning vector pICH36166 (FIG. 15) was cut with PstI and column-purified, too. The cloning reaction was set up with 1.5 µl vector (ca. 40 ng), 4 µl PCR-product, 2 µl 10× T4 polymerase buffer and 0.5 µl T4 DNA polymerase (NEB) in a total volume of 20 µl. The reaction was incubated 5 min at room temperature and then transformed completely into 100 µl chemically competent *E. coli* DH10b cells using heat shock transformation. Transformed cells were selected on medium supplemented with X-gal. White colonies were screened by colony-PCR (using two primers in the cloning vector flanking the insertion, kanseqf and kanseqr) for presence and size of the insert (FIG. 16). Using pre-amplification (1b, 1c, 2b, 2c), all tested colonies carried an insert of variable size (ca. 100-800 bp), even when using the product from the 1$^{st}$ PCR (1b, 1c). In contrast, efficient cloning of samples without pre-amplification was only possible after the nested PCR (2a vs. 1a).

Plasmid DNA was isolated from 71 clones and inserts were sequenced. All 71 sequences identified specific products. In some cases on the gels in FIG. 16, two bands can be seen after colony-PCR screening; sequencing revealed that these are the results of two colonies that were picked together, and are in fact a mix of two colonies each with a specific insert Example 6

Figure 17:
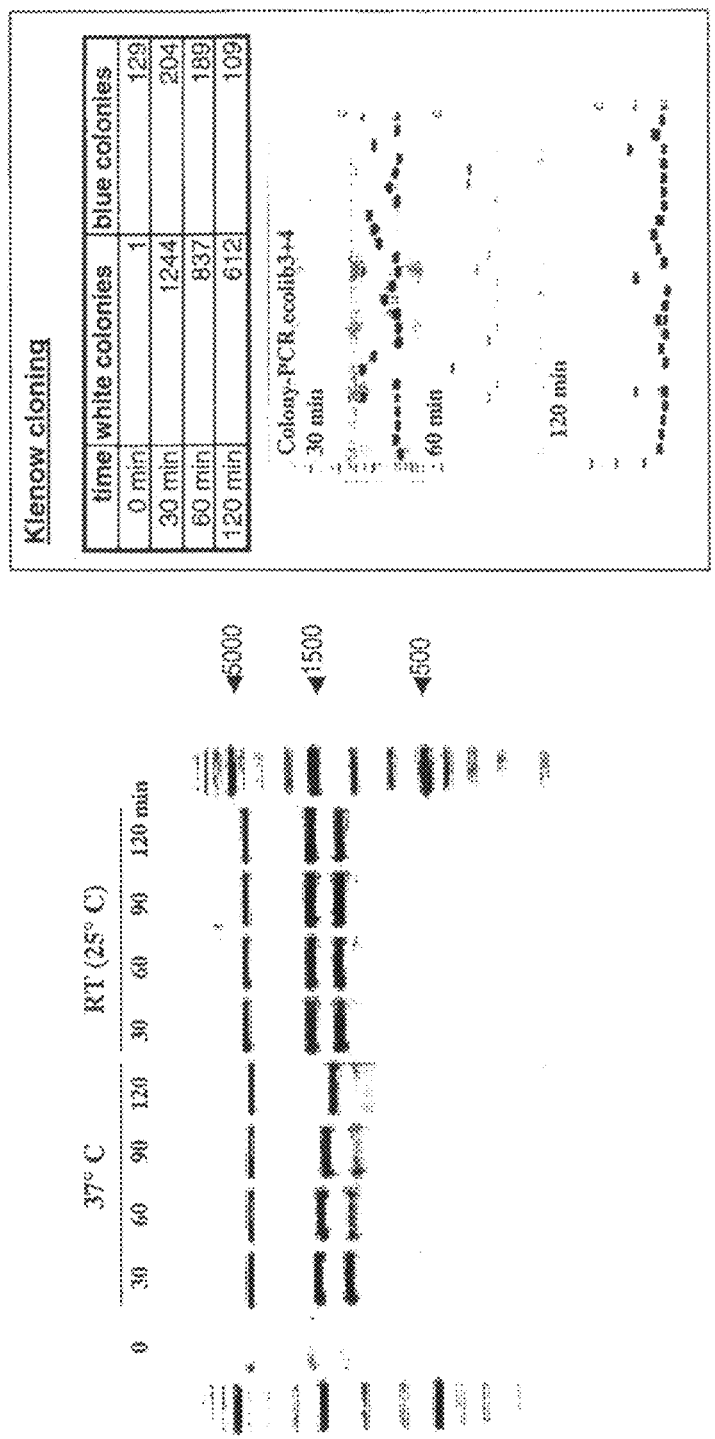
FIG. 17: Test of exonuclease activity of Klenow polymerase with different temperatures and incubation times, and cloning test. c=insert, PCR on pICH3491x (*Arabidopsis* library) ecolib3+4.

Use of Klenow for Generation of Single-Stranded DNA Ends a) Invitro Assay for Quantification of Klenow Exonuclease Activity Klenow is known to have an exonuclease activity that is much weaker than that of T4 polymerase under similar digestion conditions. To quantify this, we tested klenow exonuclease activity using the assay described above in example 3. We found that at room temperature (25° C.) no significant exonuclease activity can be detected with the assay (FIG. 17). In contrast, single-stranded regions are formed at 37° C. with incubations ranging from 30 to 90 minutes. This observation is very useful, since under standard pipetting conditions (20 to 25° C.), almost no exonuclease activity is present. This allows to pipet all samples without worrying that the first samples will be overdigested while the last samples are not yet ready. When pipeting for all samples is finished, all samples can be transferred to a water bath or thermocycler at 37° C. where a more controlled reaction will take place.

b) Test of Klenow Cloning

Cloning was performed using a library of random *Arabidopsis thaliana* fragments amplified by PCR (c on FIG. 17) in linearized cloning vector pICH31401. Homology between the insert and vector is 20 nt at one end (cgccggtctcaaggtcagct (SEQ ID NO: 21)) and 22 nt at the other end (gccaggatctgtg-gtctcaatt (SEQ ID NO: 22). The largest number of colonies was obtained with the sample for which klenow digestion was performed for 30 minutes at 37° C.

Annex

Sequence of pICH36166 (SEQ ID NO: 23)

The Bap2 sequence (gtccagagccgtccagcaa starting at the beginning) is in bold, as well as the catching sequence (cggagaattaagggagtcacgttatgaccc). The two PstI sites are in italics and underlined.

```
gtccagagccgtccagcaactgcaggcagctggcacgacaggtttcccgactggaaagcgggcagtgagcgcaacgca attaatgtgagttagctcactcattaggcaccccaggctttacactttatgcttccggctcgtatgttgtgtggaattgtgagcggata acaatttcacacaggaaacagctatgaccatgattacgccaagcttgcatgcctgcaggtcgactctagaggatccccgggta ccgagctcgaattcactggccgtcgttttacaacgtcgtgactgggaaaaccctggcgttacccaacttaatcgccttgcagcac atccccctttcgccagctggcgtaatagcgaagaggcccgcaccgatcgcccttcccaacagttgcgcagcctgaatggcga atggcgcctgatgcggtattttctccttacgcatctgtgcggtatttcacaccgcatatggtgcactctcagtacaatctgctctgatg ccgcatagttaagccagccccgacacccgccaacacccgctgacgcgccctgacgggcttgtctgctcccggcatccgctta cagacaagctgtgaccgtctccgggagctgcatgtgtcagaggttttcaccgtcatcaccgaaacgcgcgctgcagcggaga attaagggagtcacgttatgacccggtaaagtcttccacatctaggatctgccaggaaccgtaaaaaggccgcgttgctggc
```

-continued

```
gtttttccataggctccgccccctgacgagcatcacaaaaatcgacgctcaagtcagaggtggcgaaacccgacaggacta taaagatacaggcgtttccccctggaagctccctcgtgcgctctcctgttccgaccctgccgcttaccggatacctgtccgcctt ctcccttcgggaagcgtggcgctttctcatagctcacgctgtaggtatctcagttcggtgtaggtcgttcgctccaagctgggctgtg tgcacgaaccccccgttcagcccgaccgctgcgccttatccggtaactatcgtcttgagtccaacccggtaagacacgacttat cgccactggcagcagccactggtaacaggattagcagagcgaggtatgtaggcggtgctacagagttcttgaagtggtggcct aactacggctacactagaaggacagtatttggtatctgcgctctgctgaagccagttaccttcggaaaaagagttggtagctcttg atccggcaaacaaaccaccgctggtagcggtggttttttgtttgcaagcagcagattacgcgcagaaaaaaggatctcaag aagatcctttgatcttttctacggggtctgacgctcagtggaacgaaaactcacgttaagggattttggtcatgagattatcaaaa ggatcttcacctagatccttttaaattaaaaatgaagttttaaatcaatctaaagtatatatgagtaaacttggtctgacagttaccaa tgcttaatcagtgaggcacctatctcagcgatctgtctatttcgttcatccatagttgcctgactccccgtcgtgtagataactacgat acgggagggcttaccatctggccccagtgctgcaatgataccgcgagacccacgctcaccggctccagatttatcagcaata aaccagccagccggaagggccgagcgcagaagtggtcctgcaactttatccgcctccatccagtctattaattgttgccggga agctagagtaagtagttcgccagttaatagtttgcgcaacgttgttgccattgctacaggcatcgtggtgtcacgctcgtcgtttggt atggcttcattcagctccggttcccaacgatcaaggcgagttacatgatccccatgttgtgcaaaaaagcggttagctccttcgg tcctccgatcgttgtcagaagtaagttggccgcagtgttatcactcatggttatggcagcactgcataattctcttactgtcatgccat ccgtaagatgcttttctgtgactggtgagtactcaaccaagtcattctgagaatagtgtatgcggcgaccgagttgctcttgcccgg cgtcaatacgggataataccgcgccacatagcagaactttaaaagtgctcatcattggaaaacgttcttcggggcgaaaactct caaggatcttaccgctgttgagatccagttcgatgtaacccactcgtgcacccaactgatcttcagcatcttttactttcaccagcgt ttctgggtgagcaaaaacaggaaggcaaaatgccgcaaaaaagggaataagggcgacacggaaatgttgaatactcatac tcttcxtttttcaatattattgaagcatttatcagggttattgtctcatgagcggatacatatttgaatgtatttagaaaaataaacaaat agggttccgcgcacgaattggccagcgctgccattttgggtgaggccgttcgcggccgaggggcgcagcccctgggggg atgggaggcccgcgttagcgggccgggagggttgaagactt
```

The invention claimed is:

1. A process of inserting a nucleic acid sequence of interest into an acceptor nucleic acid, comprising the following steps:
  (i) amplifying by PCR a DNA, said DNA comprising in the following order a sequence segment U, a nucleic acid sequence segment of known nucleotide sequence K2 and a nucleic acid sequence segment of known sequence K3, said PCR using a forward primer defining a first end of the amplified DNA and a reverse primer defining a second end of the amplified DNA, said reverse primer terminating at its 3'-end in a nucleotide sequence of nucleic acid sequence segment K3;
  (ii) treating said DNA amplified in the previous step, said DNA being linear double-stranded and comprising in the following order said sequence segment U, said nucleic acid sequence segment of known nucleotide sequence K2 and said nucleic acid sequence segment of known sequence K3, with an exonuclease to obtain a single-stranded overhang at the first end of the DNA and a single-stranded overhang comprising nucleic acid segments K2 and K3 at the second end of the DNA;
  (iii) annealing the DNA obtained in the previous step and having the single-stranded overhangs at the first and the second end thereof as defined in step (ii) to a linearized double-stranded acceptor nucleic acid having at a first end thereof a single-stranded overhang complementary to the single-stranded overhang of the first end of the DNA and at a second end thereof a single-stranded overhang complementary to the single-stranded sequence segment K2 of the second end of the DNA, wherein segment K3 is not inserted into the acceptor nucleic acid; and
  (iv) transforming the reaction product obtained in the previous step into a host cell.

2. The process according to claim 1, wherein the nucleic acid sequence segment K3 is introduced into the amplified DNA by the reverse primer.

3. The process according to claim 1, wherein the primer binding sequence is a homooligomeric nucleotide sequence segment attached using terminal deoxyribonucleotide transferase.

4. The process according to claim 1, wherein said forward primer comprises an adaptor sequence segment and a sequence segment complementary to the primer binding sequence.

5. The process according to claim 1, wherein said acceptor nucleic acid does not contain a sequence portion of more than 7 contiguous nucleotides complementary to single-stranded sequence segment K3 in the single-stranded overhang at the second end of the acceptor nucleic acid.

6. The process according to claim 1, wherein the exonuclease is E. coli T4 DNA polymerase, the large fragment of E. coli polymerase I large fragment, lambda nuclease, T7 nuclease or exonuclease III.

7. The process according to claim 1, wherein a pre-amplification step is performed by PCR before said PCR reaction defined in claim 1, using a forward primer defining the first end of the PCR product of the pre-amplification step and a reverse primer terminating at its 3'-end in a nucleotide sequence of nucleic acid sequence segment K3.

8. The process according to claim 1, wherein said attaching is performed in a mixture comprising genomic DNA isolated from eukaryotic or prokaryotic cells.

9. The process according to claim 1, wherein said attaching is performed at the 3'-end of a cDNA retro-transcribed from an mRNA.

10. A process of inserting a nucleic acid sequence of interest comprising a nucleic acid sequence segment U of unknown nucleotide sequence into an acceptor nucleic acid, comprising the following steps:
   (i) attaching a primer binding sequence to a nucleic acid sequence comprising, in the following order, the nucleic acid sequence segment U at the first end of the nucleic acid sequence, a nucleic acid sequence segment of known sequence K2 and a nucleic acid sequence segment of known sequence K3;
   (ii) amplifying by PCR a DNA, said DNA comprising in the following order the nucleic acid sequence segment U, nucleic acid sequence segment K2 and nucleic acid sequence segment K3, said PCR using a forward primer hybridizing to the primer binding sequence and defining a first end of the amplified DNA, and a reverse primer defining a second end of the amplified DNA, said reverse primer terminating at its 3'-end in a nucleotide sequence of sequence segment K3;
   (iii) treating said DNA amplified in the previous step, said DNA being linear double-stranded and comprising in the following order said sequence segment U, said nucleic acid sequence segment of known nucleotide sequence K2 and said nucleic acid sequence segment of known sequence K3 an exonuclease to obtain a single-stranded overhang at the first end of the DNA and a single-stranded overhang comprising nucleic acid segments K2 and K3 at the second end of the DNA;
   (iv) annealing the DNA obtained in the previous step and having the single-stranded overhangs at the first and the second end thereof as defined in step (iii) to a linearized double-stranded acceptor nucleic acid having at a first end thereof a single-stranded overhang complementary to the single-stranded overhang of the first end of the DNA and at a second end thereof a single-stranded overhang complementary to the single-stranded sequence segment K2 of the second end of the DNA; and
   (v) transforming the reaction product obtained in the previous step into a host cell.

11. A process of inserting a nucleic acid sequence of interest comprising a nucleic acid sequence segment U of unknown nucleotide sequence into an acceptor nucleic acid, comprising the following steps:
   (i) attaching an adaptor sequence to a nucleic acid sequence comprising, in the following order, the nucleic acid sequence segment U at the first end of the nucleic acid sequence, a nucleic acid sequence segment of known sequence K2 and a nucleic acid sequence segment of known sequence K3;
   (ii) amplifying by PCR a DNA, said DNA comprising in the following order an adaptor sequence, the nucleic acid sequence segment U, nucleic acid sequence segment K2 and nucleic acid sequence segment K3, said PCR using a forward primer defining a first end of the amplified DNA and a reverse primer defining a second end of the amplified DNA, said reverse primer terminating at its 3'-end in a nucleotide sequence of sequence segment K3;
   (iii) treating said DNA amplified in the previous step, said DNA being linear double-stranded and comprising in the following order said sequence segment U, said nucleic acid sequence segment of known nucleotide sequence K2 and said nucleic acid sequence segment of known sequence K3 an exonuclease to obtain a single-stranded overhang comprising the adaptor sequence at the first end of the DNA and a single-stranded overhang comprising nucleic acid segments K2 and K3 at the second end of the DNA;
   (iv) annealing the DNA obtained in the previous step and having the single-stranded overhangs at the first and the second end thereof as defined in step (iii) to a linearized double-stranded acceptor nucleic acid having at a first end thereof a single-stranded overhang complementary to the single-stranded overhang of the first end of the DNA and at a second end thereof a single-stranded overhang complementary to the single-stranded sequence segment K2 of the second end of the DNA; and
   (v) transforming the reaction product obtained in the previous step into a host cell.

12. A process of inserting a cDNA of an RNA sequence of interest into an acceptor nucleic acid, comprising the following steps:
   (i) isolating RNA from a cell;
   (ii) retro-transcribing RNA to form a cDNA non-coding strand;
   (iii) amplifying by PCR a DNA, said DNA comprising in the following order a sequence segment U, a nucleic acid sequence segment of known sequence K2 and a nucleic acid sequence segment of known sequence K3, said PCR using a forward primer defining a first end of the amplified DNA and a reverse primer defining a second end of the amplified DNA, said reverse primer terminating at its 3'-end in a nucleotide sequence of sequence segment K3;
   (iv) treating said DNA amplified in the previous step, said DNA being linear double-stranded and comprising in the following order said sequence segment U, said nucleic acid sequence segment of known nucleotide sequence K2 and said nucleic acid sequence segment of known sequence K3, with an exonuclease to obtain a single-stranded overhang at the first end of the DNA and a single-stranded overhang comprising nucleic acid segments K2 and K3 at the second end of the DNA;
   (v) annealing the DNA obtained in the previous step and having the single-stranded overhangs at the first and the second end thereof as defined in step (iv) to a linearized double-stranded acceptor nucleic acid having at a first end thereof a single-stranded overhang complementary to the single-stranded overhang of the first end of the DNA and at a second end thereof a single-stranded overhang complementary to the single-stranded sequence segment K2 of the second end of the DNA; and
   (vi) transforming the reaction product obtained in the previous step into a host cell.

13. The process according to claim 12, comprising providing a template for said PCR by attaching a primer binding sequence to the 3'-end of said cDNA, wherein the forward primer used in said PCR hybridizes to said primer binding sequence.

14. The process according to claim 12, wherein the RNA is mRNA.

15. The process according to claim 12, wherein the RNA encodes an immunoglobulin chain, sequence U is part of a variable region of the immunoglobulin, and the known sequences K2 and K3 are part of a constant region of the immunoglobulin.

16. The process according to claim 1, wherein the sequence of interest that is inserted into the acceptor nucleic acid comprises in 5' to 3'-direction a sequence segment U and a sequence segment K2 of known nucleotide sequence, and does not comprise sequence segment K3 of the reverse primer.

17. The process according to claim 1, wherein said nucleic acid sequence segment K3 of said amplified DNA consists of the nucleotide sequence of said reverse primer.

* * * * *

UNITED STATES PATENT AND TRADEMARK OFFICE
CERTIFICATE OF CORRECTION

| | | |
|---|---|---|
| PATENT NO. | : 8,883,420 B2 | Page 1 of 1 |
| APPLICATION NO. | : 13/121019 | |
| DATED | : November 11, 2014 | |
| INVENTOR(S) | : Marillonnet et al. | |

It is certified that error appears in the above-identified patent and that said Letters Patent is hereby corrected as shown below:

IN THE CLAIMS

Column 39,
Line 34, after "K3" insert --, with--.

Column 40,
Line 6, after "K3" insert --, with--.

Signed and Sealed this
Twenty-fourth Day of February, 2015

Michelle K. Lee
*Deputy Director of the United States Patent and Trademark Office*

SEQUENCE LISTING

<160> NUMBER OF SEQ ID NOS: 23

<210> SEQ ID NO 1
<211> LENGTH: 10
<212> TYPE: DNA
<213> ORGANISM: Artificial
<220> FEATURE:
<223> OTHER INFORMATION: G-tail

<400> SEQUENCE: 1 ggggggggggg                                                              10

<210> SEQ ID NO 2
<211> LENGTH: 30
<212> TYPE: DNA
<213> ORGANISM: Artificial
<220> FEATURE:
<223> OTHER INFORMATION: sequence for homology annealing

<400> SEQUENCE: 2
cggagaatta agggagtcac gttatgaccc                                          30

<210> SEQ ID NO 3
<211> LENGTH: 312
<212> TYPE: DNA
<213> ORGANISM: Artificial
<220> FEATURE:

<223> OTHER INFORMATION: sequence portion of IgM, heavy chain, constant
      region

<400> SEQUENCE: 3
gggagtgcat ccgccccaac ccttttcccc ctcgtctcct gtgagaattc cccgtcggat    60
acgagcagcg tggccgttgg ctgcctcgca caggacttcc ttcccgactc catcacttts   120
tcctggaaat acaagaacaa ctctgacatc agcagyaccc ggggcttccc atcagtcctg   180 agaggggca agtacgcagc cacctcacag gtgctgctgc cttccaagga cgtcatgcag    240
ggcacagacg aacacgtggt gtgcaaagtc agcaccccca acggcaacaa agaaaagaac   300
gtgcctcttc ca                                                      312

<210> SEQ ID NO 4
<211> LENGTH: 320
<212> TYPE: DNA
<213> ORGANISM: Artificial
<220> FEATURE:
<223> OTHER INFORMATION: sequence portion of IgM, light chain, constant
      region

<400> SEQUENCE: 4
gaactgtggc tgcaccatct gtcttcatct tcccgccatc tgatgagcag ttgaaatctg    60
gaactgcctc tgttgtgtgc ctgctgaata acttctatcc cagagaggcc aaagtacagy   120
ggaaggtgga taacgccctc caatcgggta actcccagga gagtgtcaca gagcaggasa   180
gcaaggacag cacctacagc ctcagcarca ccctgacgct gagcaaagca gactacgaga   240
aacacaaagt ctacgcctgc gaagtcaccc atcagggcct gagctcgccc gtcacaaaga   300
gcttcaacag gggagagtgt                                              320

<210> SEQ ID NO 5
<211> LENGTH: 25
<212> TYPE: DNA
<213> ORGANISM: Artificial
<220> FEATURE:
<223> OTHER INFORMATION: sequence for annealing by homology

<400> SEQUENCE: 5
ttaacaggtg atccaggaaa taagg                                         25

<210> SEQ ID NO 6
<211> LENGTH: 62
<212> TYPE: DNA
<213> ORGANISM: Artificial
<220> FEATURE:
<223> OTHER INFORMATION: PCR primer IgcIon1

<400> SEQUENCE: 6
ggagggttga agacttgtcc agagccgtcc agcaactgca ggcagctggc acgacaggtt    60
tc                                                                  62

<210> SEQ ID NO 7
<211> LENGTH: 81
<212> TYPE: DNA
<213> ORGANISM: Artificial
<220> FEATURE:
<223> OTHER INFORMATION: PCR primer nospclon1

<400> SEQUENCE: 7
gatcctagat gtggaagact ttaccgggtc ataacgtgac tcccttaatt ctccgctgca    60
gcgcgcgttt cggtgatgac g                                             81

<210> SEQ ID NO 8
<211> LENGTH: 20
<212> TYPE: DNA
<213> ORGANISM: Artificial
<220> FEATURE:
<223> OTHER INFORMATION: primer Bap2

<400> SEQUENCE: 8
gtccagagcc gtccagcaac                                          20

<210> SEQ ID NO 9
<211> LENGTH: 33
<212> TYPE: DNA
<213> ORGANISM: Artificial
<220> FEATURE:
<223> OTHER INFORMATION: PCR primer Bap2pc

<400> SEQUENCE: 9
gtccagagcc gtccagcaac cccccccccc ccc                           33

<210> SEQ ID NO 10
<211> LENGTH: 19
<212> TYPE: DNA
<213> ORGANISM: Artificial
<220> FEATURE:
<223> OTHER INFORMATION: PCR primer Mu2N

<400> SEQUENCE: 10
tctgctgatg tcagagttg                                           19

<210> SEQ ID NO 11
<211> LENGTH: 18
<212> TYPE: DNA
<213> ORGANISM: Artificial
<220> FEATURE:
<223> OTHER INFORMATION: PCR primer Mu3N

<400> SEQUENCE: 11
aagtcctgtg cgaggcag                                            18

<210> SEQ ID NO 12
<211> LENGTH: 21
<212> TYPE: DNA
<213> ORGANISM: Artificial
<220> FEATURE:
<223> OTHER INFORMATION: PCR primer KC2N

<400> SEQUENCE: 12
ggagggcgtt atccaccttc c                                        21

<210> SEQ ID NO 13
<211> LENGTH: 21
<212> TYPE: DNA
<213> ORGANISM: Artificial
<220> FEATURE:
<223> OTHER INFORMATION: PCR primer KC3N

<400> SEQUENCE: 13
tcagcaggca cacaacagag g                                        21

<210> SEQ ID NO 14
<211> LENGTH: 20
<212> TYPE: DNA
<213> ORGANISM: Artificial
<220> FEATURE:

```
<223> OTHER INFORMATION: PCR primer 3'-NTRf1

<400> SEQUENCE: 14
gcgcacgata gcgcatagtg                                              20

<210> SEQ ID NO 15
<211> LENGTH: 21
<212> TYPE: DNA
<213> ORGANISM: Artificial
<220> FEATURE:
<223> OTHER INFORMATION: PCR primer 3'-NTRf2

<400> SEQUENCE: 15
atccgtaggg gtggcgtaaa c                                            21

<210> SEQ ID NO 16
<211> LENGTH: 20
<212> TYPE: DNA
<213> ORGANISM: Artificial
<220> FEATURE:
<223> OTHER INFORMATION: PCR primer kanseqf

<400> SEQUENCE: 16
tggaaaaacg ccagcaacgc                                              20

<210> SEQ ID NO 17
<211> LENGTH: 20
<212> TYPE: DNA
<213> ORGANISM: Artificial
<220> FEATURE:
<223> OTHER INFORMATION: PCR primer kanser

<400> SEQUENCE: 17
tgtctcatga gcggatacat                                              20

<210> SEQ ID NO 18
<211> LENGTH: 29
<212> TYPE: DNA
<213> ORGANISM: Artificial
<220> FEATURE:
<223> OTHER INFORMATION: PCR primer nospromfwd

<400> SEQUENCE: 18
tttgctagct gatagtgacc ttaggcgac                                    29

<210> SEQ ID NO 19
<211> LENGTH: 23
<212> TYPE: DNA
<213> ORGANISM: Artificial
<220> FEATURE:
<223> OTHER INFORMATION: PCR primer nosprev2

<400> SEQUENCE: 19
tgcggttctg tcagttccaa acg                                          23

<210> SEQ ID NO 20
<211> LENGTH: 19
<212> TYPE: DNA
<213> ORGANISM: Artificial
<220> FEATURE:
<223> OTHER INFORMATION: PCR primer bvipcr3

<400> SEQUENCE: 20
cggcttgtcc cgcgtcatc                                               19
```

```
<210> SEQ ID NO 21
<211> LENGTH: 20
<212> TYPE: DNA
<213> ORGANISM: Artificial
<220> FEATURE:
<223> OTHER INFORMATION: sequence of homology

<400> SEQUENCE: 21
cgccggtctc aaggtcagct                                                 20

<210> SEQ ID NO 22
<211> LENGTH: 22
<212> TYPE: DNA
<213> ORGANISM: Artificial
<220> FEATURE:
<223> OTHER INFORMATION: sequence of homology

<400> SEQUENCE: 22
gccaggatct gtggtctcaa tt                                              22

<210> SEQ ID NO 23
<211> LENGTH: 2591
<212> TYPE: DNA
<213> ORGANISM: Artificial
<220> FEATURE:
<223> OTHER INFORMATION: sequence of plasmid pICH36166

<400> SEQUENCE: 23
gtccagagcc gtccagcaac tgcaggcagc tggcacgaca ggtttcccga ctggaaagcg      60
ggcagtgagc gcaacgcaat taatgtgagt tagctcactc attaggcacc ccaggcttta     120
cactttatgc ttccggctcg tatgttgtgt ggaattgtga gcggataaca atttcacaca     180
ggaaacagct atgaccatga ttacgccaag cttgcatgcc tgcaggtcga ctctagagga     240
tccccgggta ccgagctcga attcactggc cgtcgtttta caacgtcgtg actgggaaaa     300
ccctggcgtt acccaactta atcgccttgc agcacatccc cctttcgcca gctggcgtaa     360
tagcgaagag gcccgcaccg atcgcccttc ccaacagttg cgcagcctga atggcgaatg     420
gcgcctgatg cggtattttc tccttacgca tctgtgcggt atttcacacc gcatatggtg     480
cactctcagt acaatctgct ctgatgccgc atagttaagc cagccccgac acccgccaac     540
acccgctgac gcgccctgac gggcttgtct gctcccggca tccgcttaca gacaagctgt     600
gaccgtctcc gggagctgca tgtgtcagag gttttcaccg tcatcaccga aacgcgcgct     660
gcagcggaga attaagggag tcacgttatg acccggtaaa gtcttccaca tctaggatct     720
gccaggaacc gtaaaaaggc cgcgttgctg cgttttttcc ataggctccg cccccctgac     780
gagcatcaca aaaatcgacg ctcaagtcag aggtggcgaa acccgacagg actataaaga     840
taccaggcgt ttccccctgg aagctccctc gtgcgctctc ctgttccgac cctgccgctt     900
accggatacc tgtccgcctt tctcccttcg ggaagcgtgg cgctttctca tagctcacgc     960
tgtaggtatc tcagttcggt gtaggtcgtt cgctccaagc tgggctgtgt gcacgaaccc    1020
cccgttcagc ccgaccgctg cgccttatcc ggtaactatc gtcttgagtc aacccggta    1080 agacacgact tatcgccact ggcagcagcc actggtaaca ggattagcag agcgaggtat    1140
gtaggcggtg ctacagagtt cttgaagtgg tggcctaact acggctacac tagaaggaca    1200
gtatttggta tctgcgctct gctgaagcca gttaccttcg gaaaaagagt tggtagctct    1260
tgatccggca acaaaccac cgctggtagc ggtggttttt ttgtttgcaa gcagcagatt    1320
acgcgcagaa aaaaaggatc tcaagaagat cctttgatct tttctacggg gtctgacgct    1380
```

```
cagtggaacg aaaactcacg ttaagggatt ttggtcatga gattatcaaa aaggatcttc   1440
acctagatcc tttaaatta aaaatgaagt tttaaatcaa tctaaagtat atatgagtaa   1500
acttggtctg acagttacca atgcttaatc agtgaggcac ctatctcagc gatctgtcta   1560
tttcgttcat ccatagttgc ctgactcccc gtcgtgtaga taactacgat acgggagggc   1620
ttaccatctg gccccagtgc tgcaatgata ccgcgagacc cacgctcacc ggctccagat   1680
ttatcagcaa taaaccagcc agccggaagg gccgagcgca gaagtggtcc tgcaacttta   1740
tccgcctcca tccagtctat taattgttgc cgggaagcta gagtaagtag ttcgccagtt   1800
aatagtttgc gcaacgttgt tgccattgct acaggcatcg tggtgtcacg ctcgtcgttt   1860
ggtatggctt cattcagctc cggttcccaa cgatcaaggc gagttacatg atcccccatg   1920
ttgtgcaaaa aagcggttag ctccttcggt cctccgatcg ttgtcagaag taagttggcc   1980
gcagtgttat cactcatggt tatggcagca ctgcataatt ctcttactgt catgccatcc   2040
gtaagatgct tttctgtgac tggtgagtac tcaaccaagt cattctgaga atagtgtatg   2100
cggcgaccga gttgctcttg cccggcgtca atacgggata ataccgcgcc acatagcaga   2160
actttaaaag tgctcatcat tggaaaacgt tcttcggggc gaaaactctc aaggatctta   2220
ccgctgttga gatccagttc gatgtaaccc actcgtgcac ccaactgatc ttcagcatct   2280
tttactttca ccagcgtttc tgggtgagca aaaacaggaa ggcaaaatgc cgcaaaaaag   2340
ggaataaggg cgacacggaa atgttgaata ctcatactct tccttttca atattattga    2400 agcatttatc agggttattg tctcatgagc ggatacatat ttgaatgtat ttagaaaaat   2460
aaacaaatag gggttccgcg cacgaattgg ccagcgctgc cattttggg gtgaggccgt    2520 tcgcggccga ggggcgcagc ccctgggggg atgggaggcc cgcgttagcg ggccgggagg   2580
gttgaagact t                                                       2591
```